United States Patent
Frasch et al.

(10) Patent No.: US 11,622,710 B2
(45) Date of Patent: Apr. 11, 2023

(54) EFFICIENT FETAL-MATERNAL ECG SIGNAL SEPARATION FROM TWO MATERNAL ABDOMINAL LEADS VIA DIFFUSION-BASED CHANNEL SELECTION

(71) Applicants: University of Washington, Seattle, WA (US); The Governing Council of the University of Toronto, Toronto (CA)

(72) Inventors: Martin G. Frasch, Seattle, WA (US); Hau-tieng Wu, Toronto (CA)

(73) Assignees: University of Washington, Seattle, WA (US); The Governing Council of the University of Toronto, Toronto (CA)

(*) Notice: Subject to any disclaimer, the term of this patent is extended or adjusted under 35 U.S.C. 154(b) by 698 days.

(21) Appl. No.: 16/490,320

(22) PCT Filed: Mar. 1, 2018

(86) PCT No.: PCT/US2018/020529
§ 371 (c)(1),
(2) Date: Aug. 30, 2019

(87) PCT Pub. No.: WO2018/160890
PCT Pub. Date: Sep. 7, 2018

(65) Prior Publication Data
US 2021/0330236 A1    Oct. 28, 2021

Related U.S. Application Data

(60) Provisional application No. 62/465,305, filed on Mar. 1, 2017.

(51) Int. Cl.
*A61B 5/344* (2021.01)
*A61B 5/327* (2021.01)
(Continued)

(52) U.S. Cl.
CPC .............. *A61B 5/344* (2021.01); *A61B 5/271* (2021.01); *A61B 5/327* (2021.01); *A61B 5/339* (2021.01);
(Continued)

(58) Field of Classification Search
CPC .......... A61B 5/344; A61B 5/327; A61B 5/271
(Continued)

(56) References Cited

U.S. PATENT DOCUMENTS 4,945,917 A * 8/1990 Akselrod ............. A61B 5/4362
                                                    600/509
5,042,499 A   8/1991 Frank et al.
(Continued)

OTHER PUBLICATIONS

Takens, F., "Detecting Strange Attractors in Turbulence," in "Dynamical Systems and Turbulence, Warwick 1980," Springer, Berlin, Heidelberg, 1981, 16 pages.
(Continued)

*Primary Examiner* — Nadia A Mahmood
(74) *Attorney, Agent, or Firm* — Christensen O'Connor Johnson Kindness PLLC

(57) ABSTRACT

In some embodiments, techniques capable of obtaining high-quality fetal ECG (fECG) information using as few as two composite (maternal and fetal) maternal abdominal ECG (aECG) signals to derive the fetal ECG information are provided. In some embodiments, maternal ECG information and fetal ECG information are both obtained from the aECG signals, and are either presented or stored. The techniques may use novel proposed diffusion-based channel selection criteria. To validate the proposed techniques, analysis results of two publicly available databases are described, and compared with other available techniques in the literature.

20 Claims, 12 Drawing Sheets

(51) Int. Cl.
    A61B 5/271    (2021.01)
    A61B 5/339    (2021.01)
    A61B 5/352    (2021.01)
    A61B 5/00     (2006.01)
(52) U.S. Cl.
    CPC ............ *A61B 5/352* (2021.01); *A61B 5/7257* (2013.01); *A61B 2560/02* (2013.01)
(58) Field of Classification Search
    USPC ........................................................ 600/511
    See application file for complete search history.

(56)             References Cited

U.S. PATENT DOCUMENTS

| | | | |
|---|---|---|---|
| 5,372,139 | A | 12/1994 | Holls et al. |
| 6,751,498 | B1 | 6/2004 | Greenberg et al. |
| 7,333,850 | B2 | 2/2008 | Marossero et al. |
| 2004/0243015 | A1 | 12/2004 | Smith et al. |
| 2009/0182242 | A1 | 7/2009 | Moses et al. |
| 2012/0108989 | A1 | 5/2012 | Gargiulo et al. |
| 2015/0208939 | A1* | 7/2015 | Zigel .................... A61B 5/7278 600/511 |

OTHER PUBLICATIONS

Talmon, R., and H.-T. Wu, "Latent Common Manifold Learning With Alternating Diffusion: Analysis and Applications," arXiv:1602.00078v1 [physics.data-an], preprint Jan. 30, 2016, 53 pages.
Varanini, M., et al., "An Efficient Unsupervised Fetal QRS Complex Detection From Abdominal Maternal ECG," Physiological Measurement 35:1607-1619, 2014.
Widrow, B., et al., "Adaptive Noise Cancelling: Principles and Applications," Proceedings of the IEEE 63(12):1692-1717, Dec. 1975.
Li, R., et al., "Efficient Fetal-Maternal ECG Signal Separation From Two Channel Maternal Abdominal ECG via Diffusion-Based Channel Selection," Frontiers in Physiology, vol. 8, Article 277, May 2017, 12 pages.
Behar, J., et al., "A Practical Guide to Non-Invasive Foetal Electrocardiogram Extraction and Analysis," Physiological Measurement 37:R1-R35, 2016.
El Karoui, N., "On Information Plus Noise Kernel Random Matrices," The Annals of Statistics 38(5):3191-3216, 2010.
Kanjilal, P.P., et al., "Fetal ECG Extraction From Single-Channel Maternal ECG Using Singular Value Decomposition," IEEE Transactions on Biomedical Engineering 44(1):51-59, Jan. 1997.
Christov, I., et al., "Extraction of the Fetal ECG in Noninvasive Recordings by Signal Decompositions," Physiological Measurement 35:1713-1721, 2014.
Vullings, R., et al., "Dynamic Segmentation and Linear Prediction for Maternal ECG Removal in Antenatal Abdominal Recordings," Physiological Measurement 30:291-307, 2009.
Agostinelli, A., et al., "Noninvasive Fetal Electrocardiography: An Overview of the Signal Electrophysiological Meaning, Recording Procedures, and Processing Techniques," Annals of Noninvasive Electrocardiology 20(4):303-313, Jul. 2015.
Clifford, G.D., et al., "Non-Invasive Fetal ECG Analysis," Physiological Measurement 35:1521-1536, 2014.
Walsh, III, J.A., et al., "Novel Wireless Devices for Cardiac Monitoring," Circulation 130:573-581, Aug. 2014.
International Search Report and Written Opinion dated Apr. 26, 2018, issued in corresponding International Application No. PCT/US2018/020529 filed Mar. 1, 2018, 9 pages.
Akbari, H., et al., "Fetal ECG Extraction Using $\pi$Tucker Decomposition," Proceedings of the 2015 International Conference on Systems, Signals and Image Processing (IWSSIP), Sep. 10-12, 2015, London, pp. 174-178.

Akhbari, M., et al., "Fetal Electrocardiogram R-Peak Detection Using Robust Tensor Decomposition and Extended Kalman Filtering," Computing in Cardiology 40:189-2013.
Amer-Wåhlin, I., et al., "Cardiotocography Only Versus Cardiotocography Plus ST Analysis of Fetal Electrocardiogram for Intrapartum Fetal Monitoring: A Swedish Randomised Controlled Trial," Lancet 358:534-538, 2001.
Anblagan, D., et al., "Association Between Preterm Brain Injury and Exposure to Chorioamnionitis During Fetal Life," Scientific Reports, vol. 6, ID 37932, 2016, pp. 1-9.
Andreotti, F., et al., "An Open-Source Framework for Stress-Testing Non-lnvasive Foetal ECG Extraction Algorithms," Physiological Measurement 7:627-648, 2016.
Andreotti, F., et al., "Robust Fetal ECG Extraction and Detection From Abdominal Leads," Physiological Measurement 35:1551-1567, 2014.
Behar, J., et al., "A Comparison of Single Channel Fetal ECG Extraction Methods," Annals of Biomedical Engineering 42(6):1340-1353, Jun. 2014.
Behar, J., et al., "Combining and Benchmarking Methods of Foetal ECG Extraction Without Maternal or Scalp Electrode Data," Physiological Measurement 35:1569-1589, 2014.
Belfort, M.A., et al., "A Randomized Trial of Intrapartum Fetal ECG ST-Segment Analysis," New England Journal of Medicine 373(7):632-641, Aug. 2015.
Bravi, A., et al., "Do Physiological and Pathological Stresses Produce Different Changes in Heart Rate Variability?" Frontiers in Physiology 4, Article 197, Jul. 2013, pp. 1-8.
Castillo, E., et al., "Efficient Wavelet-Based ECG Processing for Single-Lead FHR Extraction," Digital Signal Processing 23:1897-1909, 2013.
Coifman, R.R., and S. Lafon, "Diffusion Maps," Applied and Computational Harmonic Analysis 21:5-30, 2006.
Daubechies, I., et al., "ConceFT: Concentration of Frequency and Time via a Multitapered Synchrosqueezed Transform," Philosophical Transactions of the Royal Society A: Mathematical, Physical and Engineering Sciences 374(2065):20150193, Apr. 2016, 19 pages.
De Lathauwer, L., et al., "Fetal Electrocardiogram Extraction by Blind Source Subspace Separation," IEEE Transactions on Biomedical Engineering 47(5):567-572, May 2000.
Di Maria, C., et al., "Extracting Fetal Heart Beats From Maternal Abdominal Recordings: Selection of the Optimal Principal Components," Physiological Measurement 35:1649-1664, 2014.
Durosier, L.D., et al., "Sampling Rate of Heart Rate Variability Impacts the Ability to Detect Acidemia in Ovine Fetuses Near-Term," Frontiers in Pediatrics 2, Article 38, May 2014, pp. 1-6.
Durosier, L.D., et al., "Does Heart Rate Variability Reflect the Systemic Inflammatory Response in a Fetal Sheep Model of Lipopolysaccharide-Induced Sepsis?" Physiological Measurement 36:2089-2102, 2015.
El Karoui, N., and H.-T. Wu, "Graph Connection Laplacian Methods Can Be Made Robust to Noise," Annals of Statistics 44(1):346-372, 2016.
Fairchild, K.D., et al., "Abnormal Heart Rate Characteristics Are Associated With Abnormal Neuroimaging and Outcomes in Extremely Low Birth Weight Infants," Journal of Perinatology 34:375-379, 2014.
Fairchild, K.D., et al., "Pathogen-Induced Heart Rate Changes Associated With Cholinergic Nervous System Activation," American Journal of Physiology: Regulatory, Integrative and Comparative Physiology 300(2):R330-R339, 2011.
Garzoni, L., et al., "Fetal Cholinergic Anti-Inflammatory Pathway and Necrotizing Enterocolitis: The Brain-Gut Connection Begins in Utero," Frontiers in Integrative Neuroscience 7, Article 57, Aug. 2013, pp. 1-9.
Ghaffari, A., et al., "Robust Fetal QRS Detection From Noninvasive Abdominal Electrocardiogram Based on Channel Selection and Simultaneous Multichannel Processing," Australasian Physical & Engineering Sciences in Medicine 38(4):581-592, Dec. 2015.
Goldberger, A.L., et al., "PhysioBank, PhysioToolkit, and PhysioNet: Components of a New Research Resource for Complex Physiologic Signals," Circulation 101:e215-e220, Jun. 2000.

(56) References Cited

OTHER PUBLICATIONS

Graupe, D., et al., "Blind Adaptive Filtering for Non-Invasive Extraction of the Fetal Electrocardiogram and Its Non-Stationarities," Proceedings of the Institution of Mechanical Engineers, Part H: Journal of Engineering in Medicine 222(8):1221-1234, Nov. 2008.
Guerrero-Martínez, J.F., et al., "New Algorithm for Fetal QRS Detection in Surface Abdominal Records," Computers in Cardiology 33:441-444, 2006.
Hagberg, H., et al., "The Role of Inflammation in Perinatal Brain Injury," Nature Reviews Neurology 11(4):192-208, Apr. 2015. (Author Manuscript provided, PMCID: PMC4664161, available in PMC Nov. 30, 2015, 36 pages.).
Haghpanahi, M., and D.A. Borkholder, "Fetal ECG Extraction From Abdominal Recordings Using Array Signal Processing," Computing in Cardiology 40:173-176, 2013.
Jenkins, H.M.L., "Thirty Years of Electronic Intrapartum Fetal Heart Rate Monitoring: Discussion Paper," Journal of the Royal Society of Medicine 82:210-214, Apr. 1989.
Keller, Y., et al., "Audio-Visual Group Recognition Using Diffusion Maps," IEEE Transactions on Signal Processing 58(1):403-413, Jan. 2010.
Kotas, M., et al., "Towards Noise Immune Detection of Fetal QRS Complexes," Computer Methods and Programs in Biomedicine 97:241-256, 2010.
Laguna, P., and L. Sörnmo, "Sampling Rate and the Estimation of Ensemble Variability for Repetitive Signals," Medical and Biological Engineering and Computing 38(5):540-546, Sep. 2000.
Lederman, R.R., and R. Talmon, "Learning the Geometry of Common Latent Variables Using Alternating-Diffusion," Applied and Computational Harmonic Analysis [article in press, Sep. 2015], 28 pages.
Lee, K.J., and B. Lee, "Sequential Total Variation Denoising for the Extraction of Fetal ECG From Single-Channel Maternal Abdominal ECG," Sensors 16(7):1020, Jul. 2016, 15 pages.
Li, X., et al., "Digital Health: Tracking Physiomes and Activity Using Wearable Biosensors Reveals Useful Health-Related Information," PLOS Biology 15(1):e2001402, Jan. 2017, 30 pages.
Li, X., et al., "Sampling Frequency of Fetal Heart Rate Impacts the Ability to Predict pH and BE at Birth: A Retrospective Multi-Cohort Study," Physiological Measurement 36:L1-L12, 2015.
Lin, C.-Y., et al., "Wave-Shape Function Analysis—When Cepstrum Meets Time-Frequency Analysis," arXiv:1605.01805v2 [physics.data-an], preprint Nov. 22, 2016, 47 pages.
Liu, H.L., et al., "Can Monitoring Fetal Intestinal Inflammation Using Heart Rate Variability Analysis Signal Incipient Necrotizing Enterocolitis of the Neonate?" Pediatric Critical Care Medicine 17(4):e165-e176, Apr. 2016.
Niknazar, M., et al., "Fetal ECG Extraction by Extended State Kalman Filtering Based on Single-Channel Recordings," IEEE Transactions on Biomedical Engineering 60(5):1345-1352, May 2013.
Olofsson, P.S., et al., "Rethinking Inflammation: Neural Circuits in the Regulation of Immunity," Immunological Reviews 248:188-204, 2012.
Papyan, V., and R. Talmon, "Multimodal Latent Variable Analysis," arXiv:1611.08472v1 [cs.CV], preprint Nov. 25, 2016, 31 pages.
Da Poian, G., et al., "Sparse Representation for Fetal QRS Detection in Abdominal ECG Recordings," Proceedings of the 5th IEEE International Conference on E-Health and Biongineering—EHB 2015, Nov. 19-21, 2015, Iaşi, Romania, 4 pages.
Richter, M., et al., "Fetal ECG Extraction With Nonlinear State-Space Projections," IEEE Transactions on Biomedical Engineering 45(1):133-137, Jan. 1998.
Rodrigues, R., "Fetal Beat Detection in Abdominal ECG Recordings: Global and Time Adaptive Approaches," Physiological Measurement 35:1699-1711, 2014.
Sameni, R., "Extraction of Fetal Cardiac Signals From an Array of Maternal Abdominal Recordings," Doctoral Dissertation, Institut Polytechnique de Grenoble, Grenoble, France, Jul. 2008, 176 pages.
Sameni, R., et al., "Multichannel Electrocardiogram Decomposition Using Periodic Component Analysis," IEEE Transactions on Biomedical Engineering 55(8):1935-1940, Aug. 2008.
Singer, A., and H.-T. Wu, "Spectral Convergence of the Connection Laplacian From Random Samples," Information and Inference: A Journal of the IMA 6:58-123, 2017.
Stark, J., et al., "Takens Embedding Theorems for Forced and Stochastic Systems," Proceedings of the 2nd World Congress of Nonlear Analysts: Nonlinear Analysis, Theory, Methods & Applications 30(8):5303-5314, 1997.
Stark, J., et al., "Delay Embeddings for Forced Systems: II. Stochastic Forcing," Journal of Nonlinear Science 13:519-577, 2003.
Su, L., and H.-T. Wu, "Extract Fetal ECG From Single-Lead Abdominal ECG by De-Shape Short Time Fourier Transform and Nonlocal Median," Frontiers in Applied Mathematics and Statistics, vol. 3, Article 2, Feb. 2017, 26 pages.

\* cited by examiner

| Subject | Channel | $F_1$ (%) | MAE (msec) | PPV (%) | SE (%) |
|---|---|---|---|---|---|
| r01 | 1 and 2 | 99.45 | 1.35 | 99.22 | 99.69 |
| | 1 and 3 | 99.69 | 1.98 | 99.53 | 99.84 |
| | 1 and 4 | 99.37 | 2.44 | 99.22 | 99.53 |
| | 2 and 3 | 86.94 | 4.44 | 85.87 | 88.03 |
| | 2 and 4 | 98.74 | 2.13 | 98.59 | 98.9 |
| | 3 and 4 | 99.21 | 2.17 | 99.06 | 99.37 |
| r04 | 1 and 2 | 97.68 | 8.08 | 97.44 | 97.91 |
| | 1 and 3 | 97.52 | 8.18 | 97.28 | 97.75 |
| | 1 and 4 | 98.72 | 7.42 | 98.56 | 98.88 |
| | 2 and 3 | 98.4 | 7.78 | 98.24 | 98.56 |
| | 2 and 4 | 98.4 | 8.4 | 98.09 | 98.72 |
| | 3 and 4 | 98.72 | 7.42 | 98.56 | 98.88 |
| r07 | 1 and 2 | 98.38 | 8.68 | 98.23 | 98.54 |
| | 1 and 3 | 99.03 | 7.47 | 99.03 | 99.03 |
| | 1 and 4 | 99.84 | 8.06 | 99.84 | 99.84 |
| | 2 and 3 | 99.11 | 8.55 | 99.03 | 99.19 |
| | 2 and 4 | 99.27 | 8.59 | 99.19 | 99.35 |
| | 3 and 4 | 99.84 | 8.44 | 99.84 | 99.84 |
| r08 | 1 and 2 | 97.6 | 2.18 | 96.78 | 98.44 |
| | 1 and 3 | 99.3 | 2.22 | 98.92 | 99.69 |
| | 1 and 4 | 99.69 | 1.87 | 99.38 | 100 |
| | 2 and 3 | 28.55 | 10.63 | 34.83 | 24.18 |
| | 2 and 4 | 97.05 | 2.01 | 96.46 | 97.66 |
| | 3 and 4 | 94.36 | 4.87 | 93.43 | 95.32 |
| r10 | 1 and 2 | 98.88 | 2.85 | 98.41 | 99.36 |
| | 1 and 3 | 98.88 | 2.85 | 98.41 | 99.36 |
| | 1 and 4 | 98.88 | 2.85 | 98.41 | 99.36 |
| | 2 and 3 | 98 | 3.37 | 97.46 | 98.55 |
| | 2 and 4 | 94.67 | 4.51 | 93.7 | 95.66 |
| | 3 and 4 | 94.67 | 4.51 | 93.7 | 95.66 |

*FIG. 8*

|  | Method | mean | std | $Q_1$ | Median | $Q_3$ |
|---|---|---|---|---|---|---|
| $F_1(1)$ (%) over 6 pairs | SAVER | 99.36 | 0.52 | 98.84 | 99.69 | 99.73 |
|  | ds-AF-LMS | 99.55 | 0.74 | 99.44 | 99.84 | 99.88 |
|  | ds-ESN | 99.00 | 1.21 | 98.36 | 99.36 | 99.88 |
|  | JADE-ICA | 39.34 | 34.90 | 17.30 | 18.64 | 58.85 |
|  | PCA | 50.14 | 41.98 | 18.54 | 22.08 | 95.11 |
| MAE(1) (msec) over 6 pairs | SAVER | 4.44 | 3.05 | 1.96 | 2.85 | 7.58 |
|  | ds-AF-LMS | 4.42 | 3.02 | 2.12 | 2.49 | 7.64 |
|  | ds-ESN | 4.85 | 2.68 | 2.61 | 4.18 | 7.62 |
|  | JADE-ICA | 16.54 | 10.49 | 6.33 | 23.41 | 24.43 |
|  | PCA | 14.24 | 10.50 | 3.51 | 16.32 | 24.01 |
| $F_1(0.5)$ (%) over 6 pairs | SAVER | 98.53 | 0.79 | 98.13 | 98.44 | 99.22 |
|  | ds-AF-LMS | 98.46 | 1.69 | 98.01 | 98.91 | 99.40 |
|  | ds-ESN | 96.66 | 3.99 | 95.03 | 98.41 | 99.00 |
|  | JADE-ICA | 21.95 | 7.54 | 16.54 | 17.81 | 28.11 |
|  | PCA | 21.41 | 8.40 | 17.55 | 17.90 | 22.69 |
| MAE(0.5) (msec) over 6 pairs | SAVER | 4.78 | 3.16 | 2.19 | 3.11 | 8.07 |
|  | ds-AF-LMS | 5.09 | 2.57 | 3.18 | 3.93 | 7.80 |
|  | ds-ESN | 5.64 | 2.30 | 3.74 | 4.94 | 7.97 |
|  | JADE-ICA | 21.58 | 5.64 | 16.48 | 24.39 | 25.76 |
|  | PCA | 20.52 | 4.94 | 17.74 | 19.60 | 25.18 |

*FIG. 9*

| | Method | mean | std | $Q_1$ | Median | $Q_3$ |
|---|---|---|---|---|---|---|
| $F_1(1)$ (%) over 6 pairs | SAVER | 92.99 | 16.00 | 95.39 | 99.21 | 1 |
| | ds-AF-LMS | 72.77 | 27.52 | 51.56 | 85.50 | 98.92 |
| | ds-ESN | 72.04 | 27.61 | 50.88 | 82.54 | 99.20 |
| | JADE-ICA | 36.13 | 23.74 | 20.73 | 26.11 | 43.81 |
| | PCA | 35.35 | 23.89 | 20.16 | 24.00 | 37.97 |
| MAE(1) (msec) over 6 pairs | SAVER | 5.38 | 4.52 | 1.96 | 4.03 | 7.82 |
| | ds-AF-LMS | 7.06 | 6.13 | 2.93 | 5.36 | 7.62 |
| | ds-ESN | 6.179 | 4.59 | 2.86 | 5.54 | 7.42 |
| | JADE-ICA | 15.22 | 7.18 | 8.42 | 15.82 | 21.93 |
| | PCA | 16.04 | 7.19 | 9.59 | 18.00 | 21.75 |
| $F_1(0.5)$ (%) over 6 pairs | SAVER | 85.43 | 22.42 | 83.27 | 96.32 | 99.57 |
| | ds-AF-LMS | 56.34 | 30.51 | 25.69 | 51.55 | 90.38 |
| | ds-ESN | 58.22 | 30.85 | 36.69 | 54.55 | 89.54 |
| | JADE-ICA | 26.67 | 20.52 | 16.88 | 19.51 | 24.74 |
| | PCA | 26.59 | 21.31 | 15.96 | 19.24 | 25.19 |
| MAE(0.5) (msec) over 6 pairs | SAVER | 6.54 | 4.92 | 2.55 | 5.70 | 5.53 |
| | ds-AF-LMS | 11.63 | 8.0283 | 5.70 | 8.50 | 18.66 |
| | ds-ESN | 9.85 | 6.57 | 4.67 | 7.88 | 13.96 |
| | JADE-ICA | 20.44 | 6.46 | 16.80 | 22.17 | 24.97 |
| | PCA | 20.59 | 7.07 | 15.64 | 22.61 | 25.24 |

*FIG. 10*

|  | Channels | mean | std | $Q_1$ | Median | $Q_3$ |
|---|---|---|---|---|---|---|
| $F_1$ (%) | 1 and 2 | 98.40 | 0.79 | 97.66 | 98.38 | 99.02 |
|  | 1 and 3 | 98.88 | 0.82 | 98.54 | 99.03 | 99.40 |
|  | 1 and 4 | 99.30 | 0.49 | 98.84 | 99.37 | 99.73 |
|  | 2 and 3 | 82.20 | 30.41 | 72.34 | 98.00 | 98.58 |
|  | 2 and 4 | 97.63 | 1.85 | 96.46 | 98.4 | 98.88 |
|  | 3 and 4 | 97.36 | 2.63 | 94.59 | 98.72 | 99.37 |
| MAE (msec) | 1 and 2 | 4.63 | 3.47 | 1.98 | 2.85 | 8.23 |
|  | 1 and 3 | 4.54 | 3.02 | 2.16 | 2.85 | 7.64 |
|  | 1 and 4 | 4.53 | 2.96 | 2.30 | 2.85 | 7.58 |
|  | 2 and 3 | 6.95 | 3.00 | 4.17 | 7.78 | 9.07 |
|  | 2 and 4 | 5.13 | 3.23 | 2.10 | 4.51 | 8.45 |
|  | 3 and 4 | 5.48 | 2.49 | 3.93 | 4.87 | 7.67 |

FIG. 11

|  | Channels | Mean | std | $Q_1$ | Median | $Q_3$ |
|---|---|---|---|---|---|---|
| $F_1$ (%) | 1 and 2 | 81.69 | 25.82 | 72.60 | 95.62 | 99.36 |
|  | 1 and 3 | 82.93 | 26.28 | 83.27 | 96.24 | 99.36 |
|  | 1 and 4 | 87.93 | 22.64 | 93.08 | 97.60 | 1 |
|  | 2 and 3 | 74.40 | 30.63 | 36.10 | 93.33 | 99.67 |
|  | 2 and 4 | 81.50 | 26.64 | 66.95 | 96.51 | 99.36 |
|  | 3 and 4 | 79.83 | 28.49 | 58.78 | 96.96 | 99.67 |
| MAE (msec) | 1 and 2 | 7.72 | 7.03 | 2.53 | 5.04 | 9.32 |
|  | 1 and 3 | 7.83 | 7.45 | 2.42 | 6.08 | 8.74 |
|  | 1 and 4 | 6.21 | 6.03 | 2.04 | 4.34 | 7.66 |
|  | 2 and 3 | 9.44 | 6.88 | 4.12 | 8.05 | 12.97 |
|  | 2 and 4 | 7.93 | 6.62 | 3.61 | 6.28 | 9.67 |
|  | 3 and 4 | 7.85 | 6.85 | 2.31 | 5.92 | 9.97 |

FIG. 12

EFFICIENT FETAL-MATERNAL ECG SIGNAL SEPARATION FROM TWO MATERNAL ABDOMINAL LEADS VIA DIFFUSION-BASED CHANNEL SELECTION

CROSS-REFERENCE TO RELATED APPLICATION

This application claims the benefit of Provisional Application No. 62/465305, filed Mar. 1, 2017, the entire disclosure of which is hereby incorporated by reference in its entirety for all purposes.

BACKGROUND

Fetal electrocardiogram (ECG) and the fetal heart rate (HR) provide enormous information about fetal health, and can be used for purposes such as fetal distress monitoring. Moreover, from clinical studies and animal models, evidence is accumulating that perinatal brain injury originates in utero, yet no means exist to detect its onset early, reliably, and with simple, widely accessible means. A harbinger of brain injury is the fetal inflammatory response. There is an urgent need for early antenatal detection of fetal inflammatory response to prevent or at least mitigate the developing perinatal brain injury. In adults and neonates, complex mathematical features of heart rate fluctuations have proven promising as early diagnostic tools. For the fetal monitoring, a series of biomarkers have been developed that rely on non-invasively obtainable fetal HR. Such techniques that provide a fetal inflammatory index track inflammation along with the fetal plasma IL-6 temporal profile in a fetal sheep model of subclinical chorioamnionitis. A set of fetal HR features have also been derived that are specific to brain or gut inflammation. Such systemic and organ-specific tracking of inflammation via fetal HR is possible due to the brain-innate immune system communication reflected in the fetal HR fluctuations, commonly referred to as the cholinergic anti-inflammatory pathway.

In spite of its broad usefulness in monitoring fetal health, the technological progress in the fetal HR monitoring realm has been coming more gradually. This is, in part, due to the intrinsic limitations of the currently used fetal HR monitoring technology.

Existing techniques typically use low sampling rates traditionally used in heart rate or ECG monitoring. In animal model and human cohorts, it has been shown that low sampling rates such as these are bound to miss the faster temporal fluctuations of vagal modulations of fetal HR variability, thus leading to inaccuracies in detection of early fetal academia. A sampling rate of the ECG signal around 1000 Hz can capture these vagal influences, and this is a commonly used sampling rate for postnatal studies and the above-described work relating to a fetal inflammatory index.

Postnatal clinical studies are typically based on multi-lead ECG recordings which, even in newborns, and certainly in adults, poses no technical challenge to attach and record from. In fetuses, however, this is not the case. Since the fetal cardiac electric field strength is an order of magnitude weaker than maternal ECG signals, and given a general lack of clinical motivation in higher quality fetal HR data, little development had been done to focus on noninvasively obtaining fetal ECG (fECG) signals in clinical monitoring until the present disclosure, outside of the Doppler-based fetal HR extraction techniques that dominate the market. The Doppler-based fetal HR extraction techniques, however, suffer from low fetal HR sampling rates, largely due to the auto-correlation algorithms deployed in the devices. Trans-abdominal ECG (aECG) can machines and techniques may overcome this limitation by capturing the actual cardiac electric field, and have returned to the market during the last decade. However, their arrival has been slow, due in part to the general acceptance speed of new technology in medicine (related to regulatory and safety testing as well as the specific cultures), in part to the high cost for each device to upgrade a hospital's delivery unit, and in part to the technical difficulty of reliable and accurate fetal ECG extraction from the aECG signals.

To make the technology of high quality and low-cost fetal ECG widely accessible, techniques are desired that allow for reliable and accurate fetal ECG extraction using easily deployable aECG devices.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter. In some embodiments, a system for non-invasive measurement of heartbeat characteristics is provided. The system comprises a set of maternal abdominal leads and an abdominal electrocardiogram (aECG) device. The set of maternal abdominal leads includes a first maternal abdominal lead and a second maternal abdominal lead. The aECG device is communicatively coupled to the maternal abdominal leads and comprises at least one processor and a non-transitory computer-readable medium. The computer-readable medium has instructions stored thereon that, in response to execution by the at least one processor, cause the aECG device to measure heartbeat characteristics by creating a set of linear combinations using signals from the set of maternal abdominal leads; determining a set of rough fECGs based on the set of linear combinations; selecting a channel based on the set of rough fECGs; and measuring the heartbeat characteristics using the selected channel.

In some embodiments, a method of measuring heartbeat characteristics is provided. A computing device receives a first signal from a first maternal abdominal lead and a second signal from a second maternal abdominal lead. The computing device creates a set of linear combinations using the first signal and the second signal. The computing device determines a set of rough fECGs based on the set of linear combinations. The computing device selects a channel based on the set of rough fECGs. The computing device measures the heartbeat characteristics using the selected channel.

In some embodiments, a non-transitory computer-readable medium is provided. The non-transitory computer-readable medium has computer-executable instructions stored thereon that, in response to execution by at least one processor of an abdominal electrocardiogram (aECG) device, cause the aECG device to measure heartbeat characteristics by creating a set of linear combinations using signals from a first maternal abdominal lead and a second maternal abdominal lead; determining a set of rough fECGs based on the set of linear combinations; selecting a channel based on the set of rough fECGs; and measuring the heartbeat characteristics using the selected channel.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 8-12 are charts that provide results of testing to compare the performance of the techniques disclosed herein with previous techniques.

DETAILED DESCRIPTION

Embodiments of the present disclosure address the above challenges (and others) by providing techniques capable of obtaining high-quality fetal ECG (fECG) information from two composite (maternal and fetal) aECG signals to derive the fetal ECG information. The techniques may use currently developed single-lead fECG technique based on modern time-frequency analysis and manifold learning techniques, and a novel proposed diffusion-based channel selection criteria. All of the disclosed methods have rigorous mathematical backups, and numerically they can be efficiently implemented to handle long signal. To validate the proposed techniques, analysis results of two publicly available databases are described, and compared with other available techniques in the literature.

The disclosed techniques provide numerous benefits, including the technical benefit of newly enabling a computing device to obtain fetal ECG information and maternal ECG information from merely two maternal abdominal leads. This is a new capability which computing devices were not capable of performing before the presently disclosed techniques. Further, using maternal abdominal leads allows the technique to be noninvasive, and enabling the generation of both fetal ECG information and maternal ECG information using as few as two maternal abdominal leads makes the system simpler and easier to apply to a patient.

Figure 1:
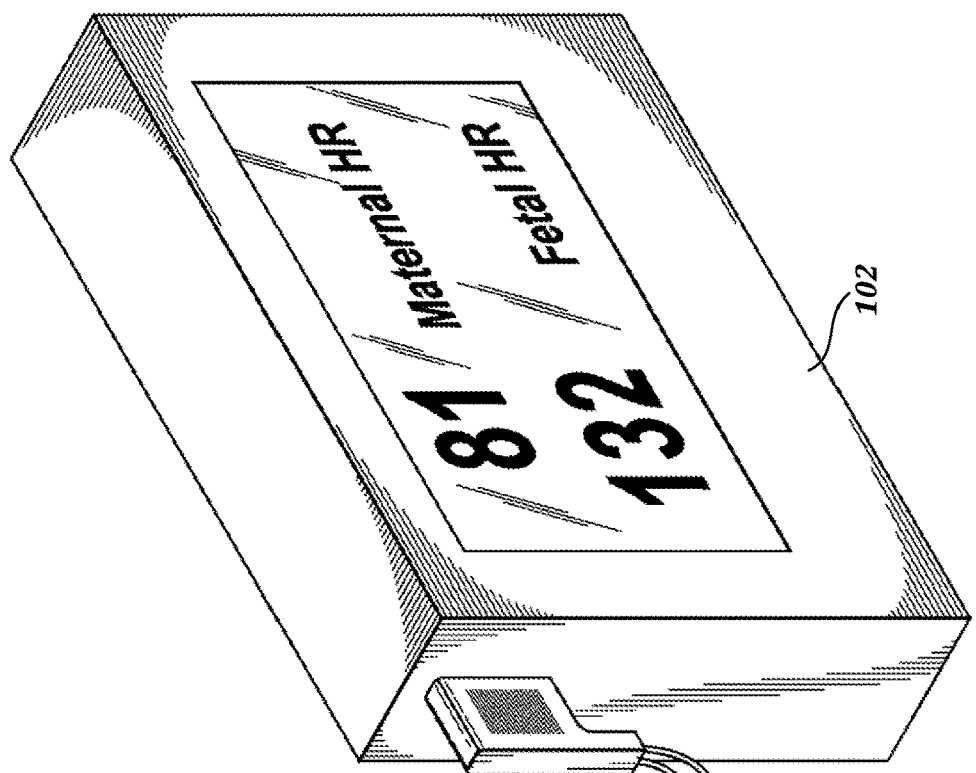
FIG. 1 is a schematic diagram that illustrates an example embodiment of a system for measuring maternal and/or fetal heartbeat characteristics using abdominal leads according to various aspects of the present disclosure.
Figure 1:
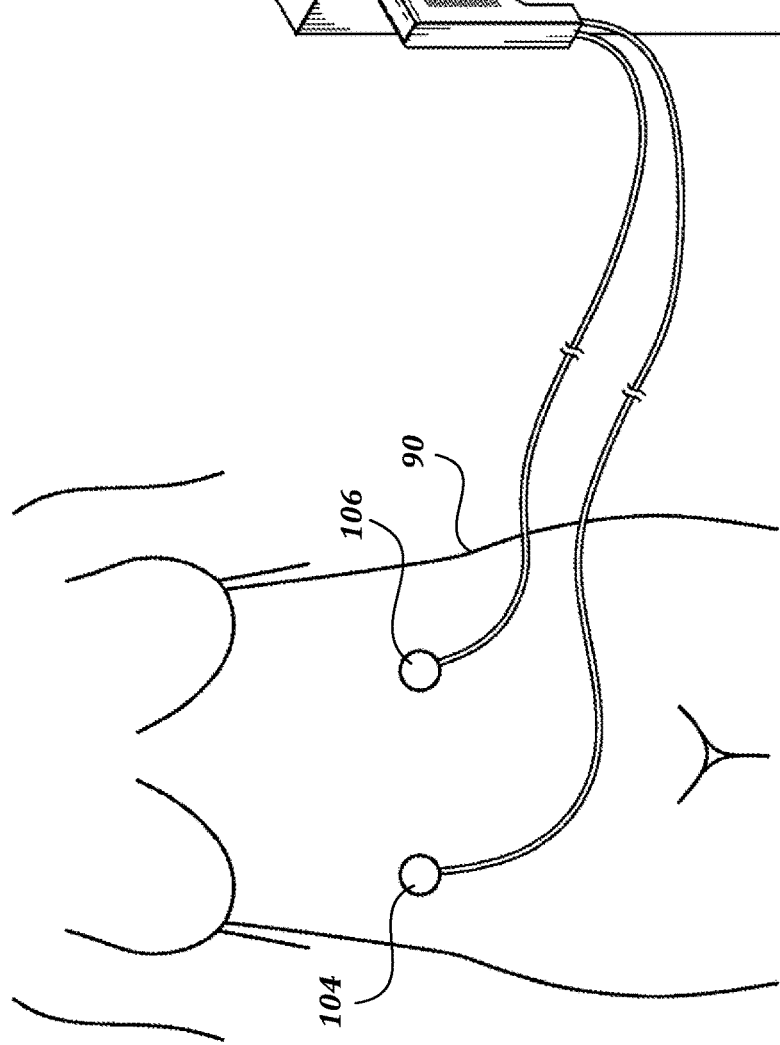

FIG. 1 is a schematic diagram that illustrates an example embodiment of a system for measuring maternal and/or fetal heartbeat characteristics using abdominal leads according to various aspects of the present disclosure. As shown, an abdominal ECG (aECG) device 102 is communicatively coupled to a first maternal abdominal lead 104 and a second maternal abdominal lead 106. The leads 104, 106 are applied to the abdomen of a pregnant woman 90. In some embodiments, the aECG device 102 uses techniques that can obtain fetal heartbeat characteristics and/or maternal heartbeat characteristics simply from the signals received from the two leads 104, 106. In some embodiments, the aECG device 102 may then present the maternal heartbeat characteristics, the fetal heartbeat characteristics, or both, on a display device. In some embodiments, the aECG device 102 may store the heartbeat characteristics in a data store, instead of or in addition to displaying the heartbeat characteristics. While the aECG device 102 uses signals from two leads 104, 106 for its calculations, in some embodiments, the aECG device 102 may be coupled to more than two leads 104, 106, and may select signals from the pair of leads that provides the best results, as described further below. FIG. 1 illustrates the aECG device 102 as a self-contained medical device, though in other embodiments, the actions of the aECG device 102 may be performed by another type of device, including but not limited to a laptop computing device, a desktop computing device, a mobile phone computing device, a tablet computing device, a server computing device, and a cloud computing service.

Figure 2:
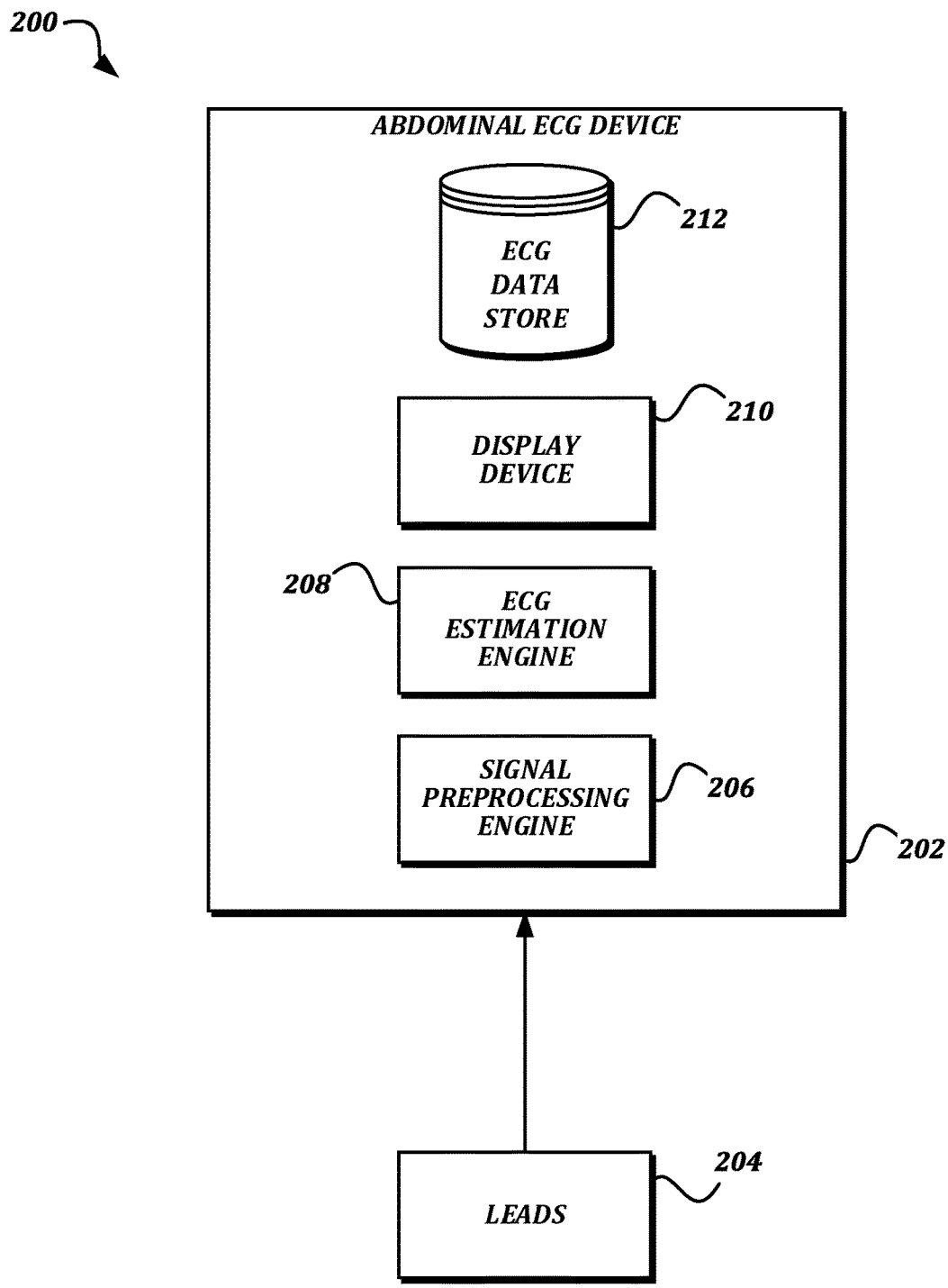
FIG. 2 is a block diagram that illustrates an example embodiment of an abdominal ECG device according to various aspects of the present disclosure.

FIG. 2 is a block diagram that illustrates an example embodiment of an abdominal ECG device according to various aspects of the present disclosure. As illustrated, the system 200 includes an abdominal ECG device 202 and a set of leads 204. The leads 204 are devices configured to detect an electrical potential, and are communicatively coupled to the abdominal ECG device 202 using any suitable technique. In some embodiments, the leads 204 are communicatively coupled to the abdominal ECG device 202 via a conductive wire. In some embodiments, the leads 204 are coupled to the abdominal ECG device 202 via a wired or wireless network, including but not limited to Ethernet, Wi-Fi, and Bluetooth. As illustrated in FIG. 1, the leads 204 are configured to be applied to a maternal abdomen.

As illustrated, the abdominal ECG device includes a signal preprocessing device 206, an ECG estimation engine 208, a display device 210, and an ECG data store 212. In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, and/or the like. An engine may be compiled into executable programs or written in interpreted programming languages. Software engines may be callable from other engines or from themselves. Generally, the engines described herein refer to logical engines that can be merged with other engines, or can be divided into sub-engines. The engines can be stored in any type of computer-readable medium or computer storage device and be stored on and executed by one or more general purpose computers, thus creating a special purpose computer configured to provide the engine.

As understood by one of ordinary skill in the art, a "data store" as described herein may be any suitable device configured to store data for access by a computing device. One example of a data store is data stored in an organized manner on a computer-readable storage medium, as described further below. One such example, which includes reliable storage but also low overhead, is a file system or database management system that stores data in files (or records) on a computer readable medium such as flash memory, random access memory (RAM), hard disk drives, and/or the like. Another example is a highly reliable, high-speed relational database management system (RDBMS) executing on one or more computing devices and accessible over a high-speed network. However, any other suitable storage technique and/or device capable of storing data for access by a computing device may be used. One of ordinary skill in the art will recognize that separate data stores described herein may be combined into a single data store, and/or a single data store described herein may be separated into multiple data stores, without departing from the scope of the present disclosure.

In some embodiments, the signal preprocessing engine 206 is configured to receive raw signals from the leads 204, and to convert the raw signals into a digital time series suitable for processing by the rest of the components of the abdominal ECG device 202. In some embodiments, the ECG estimation engine 208 processes the time series information provided by the signal preprocessing engine 206 to determine characteristics of a maternal ECG, a fetal ECG, and/or both.

In some embodiments, once the ECG estimation engine 208 determines ECG characteristics, the results are provided to other components. For example, in some embodiments, the results may be provided to the display device 210 for presentation to a user. In some embodiments, the display device 210 may be incorporated into the abdominal ECG device 202, and may include an LCD screen, a video display, an indicator light, a loudspeaker, or any other type of display device suitable for presenting ECG characteristics. In some embodiments, the display device 210 may be located remotely from the abdominal ECG device 202, and the results may be provided to the display device 210 using wired or wireless networking technology. As another example, in some embodiments, the results may be provided to the ECG data store 212 for storage. In some embodiments, the ECG data store 212 may be a computer-readable medium locally accessible to the abdominal ECG device 202. In some embodiments, the ECG data store 212 may be located on a remote server or hosted in a cloud service, and the results may be provided to the ECG data store 212 via any suitable wired or wireless networking technology. Further detailed description of the actions taken by each of these components is provided below.

Figure 3:
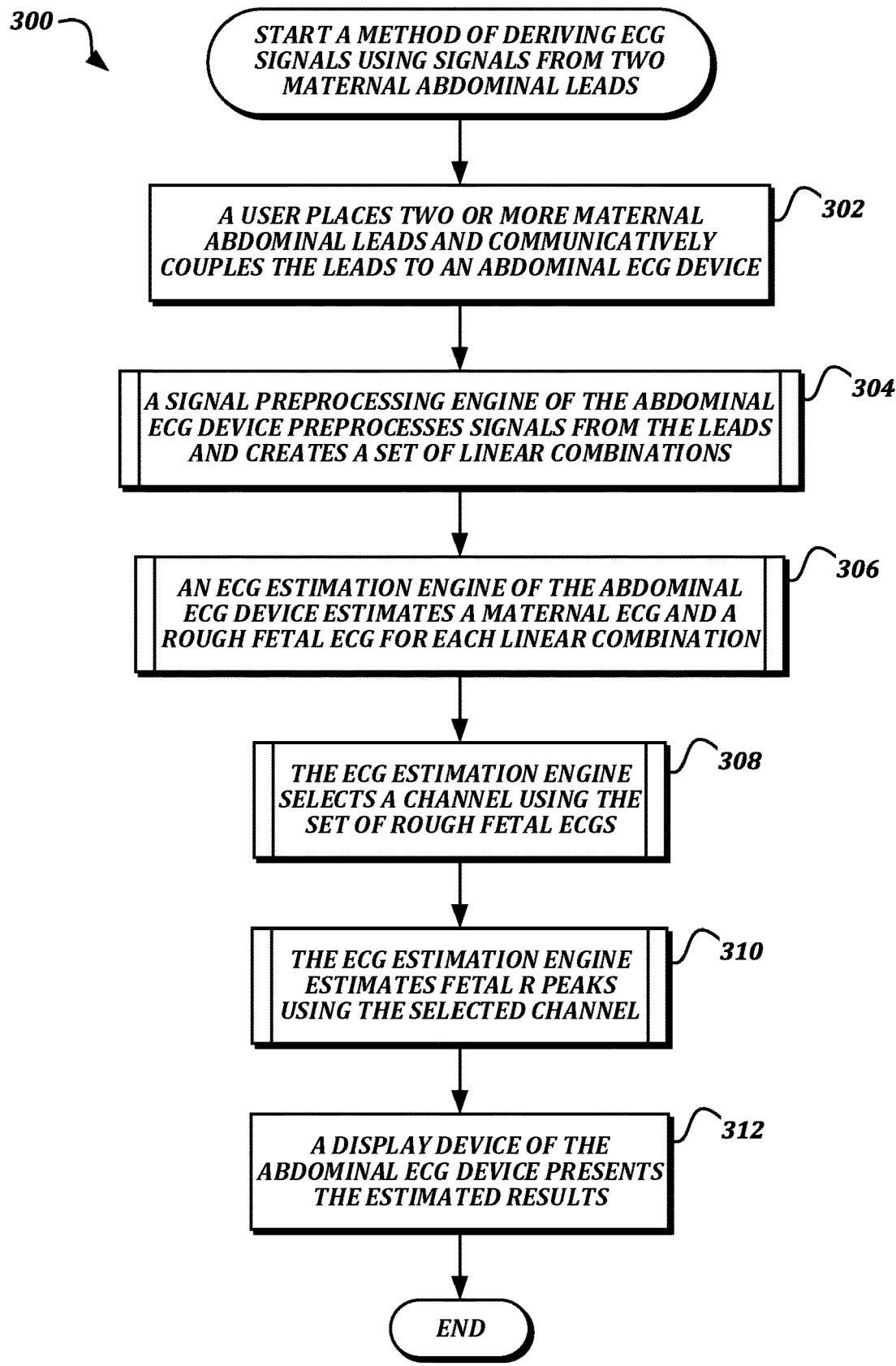
FIG. 3 is a flowchart that illustrates an example embodiment of a method of deriving ECG signals using signals from two maternal abdominal leads according to various aspects of the present disclosure.

FIG. 3 is a flowchart that illustrates an example embodiment of a method of deriving ECG signals using signals from two maternal abdominal leads according to various aspects of the present disclosure. From a start block, the method 300 proceeds to block 302, where a user places two or more maternal abdominal leads 204 and communicatively couples the leads to an abdominal ECG device 202. In some embodiments, communicatively coupling the leads 204 may include physically plugging wires from the leads 204 into the abdominal ECG device 202 or a network device through which the abdominal ECG device 202 may be reached. In some embodiments, communicatively coupling the leads 204 may include pairing the leads 204 with the abdominal ECG 202 using a wireless protocol. In some embodiments, the particular location of placement of the leads 204 on the maternal abdomen is not important, as the remainder of the method 300 is agnostic to the placement location. Though a minimum of two leads 204 may be used in order to generate linear combinations, in some embodiments, more than two leads 204 may be used in order to increase the number of pairwise linear combinations that can be generated without changing the placement of any of the leads 204.

The method 300 then advances to procedure block 304, where a procedure is performed wherein a signal preprocessing engine 206 of the abdominal ECG device 202 preprocesses signals from the leads and creates a set of linear combinations. In some embodiments, the set of linear combinations may include one or more linear combination based on each pair-wise combination of leads 204. In embodiments that use two leads 204, each of the linear combinations of the set of linear combinations would be based on those two leads. In embodiments that use, for example, three leads 204 (Lead A, Lead B, and Lead C), some of the linear combinations would be based on a combination of Lead A and Lead B, some of the linear combinations would be based on a combination of Lead A and Lead C, and some of the linear combinations would be based on a combination of Lead B and Lead C. Any suitable procedure may be used for procedure block 304, one example of which is illustrated and described with respect to FIG. 4. In some embodiments, each linear combination includes a pair of selected leads 204 and a theta ($\theta$) value used to linearly combine the signals from the pair of selected leads 204.

At procedure block 306, a procedure is performed wherein an ECG estimation engine 208 of the abdominal ECG device 202 estimates a maternal ECG and a rough fetal ECG for each linear combination. One advantage of some embodiments of the present disclosure is that, through processing of signals from as few as two maternal abdominal leads 204, both a maternal ECG and characteristics of a fetal ECG can be determined.

The procedure conducted at procedure block 306 may be used to determine the maternal ECG information. Though not illustrated in the method 300, the maternal ECG information determined in procedure block 306 may be presented by the abdominal ECG device 202 using the display device 210, may be logged within the ECG data store 212, or may be transmitted to another device for further processing. Any suitable procedure may be used for procedure block 306, one example of which is illustrated and described with respect to FIG. 5.

Next, at procedure block 308, a procedure is performed wherein the ECG estimation engine 208 selects a channel using the set of rough fetal ECGs. A channel refers to a transformation of the signals obtained from the leads 204, and in some embodiments, may include a selection of a pair of leads 204 and a theta value as described further below. Any suitable procedure may be used for procedure block 308, one example of which is illustrated and described with respect to FIG. 6. At block 310, a procedure is performed wherein the ECG estimation engine 208 estimates fetal R peaks using the selected channel. Any suitable procedure may be used for procedure block 310, one example of which is illustrated and described with respect to FIG. 7.

At block 312, a display device 210 of the abdominal ECG device 202 presents the estimated results. In some embodiments, the estimated results may include a numerical value for a fetal heartrate based on the fetal R peaks. In some embodiments, the estimated results may include indications of the fetal R peaks, such as a flashing light or a tone that coincides with the occurrence of the fetal R peaks. In some embodiments, the estimated results may be used to detect another fetal condition, such as the fetal inflammatory index mentioned above. In some embodiments, the presented results may include aspects of the maternal ECG as well, such as a heartrate or a waveform. In some embodiments, the estimated results may not be presented by the display device 210, but may instead be logged in the ECG data store 212 or transmitted to another device for storage or processing.

The method 300 then proceeds to an end block and terminates. One of ordinary skill in the art will recognize that the method 300 may operate in a continuous manner to monitor maternal and/or fetal heartbeat characteristics over time. In such embodiments, the fetus may move in relation to the leads 204 over time. Instead of moving the leads 204, the method 300 may return to block 304 to determine a new pair of leads and/or a new theta value that provides better data corresponding to the new fetal position. In some embodiments, the method 300 may continue to calculate a signal quality index (SQI, discussed further below), and may return to block 304 in response to determining that the SQI has fallen below a threshold value.

Figure 4:
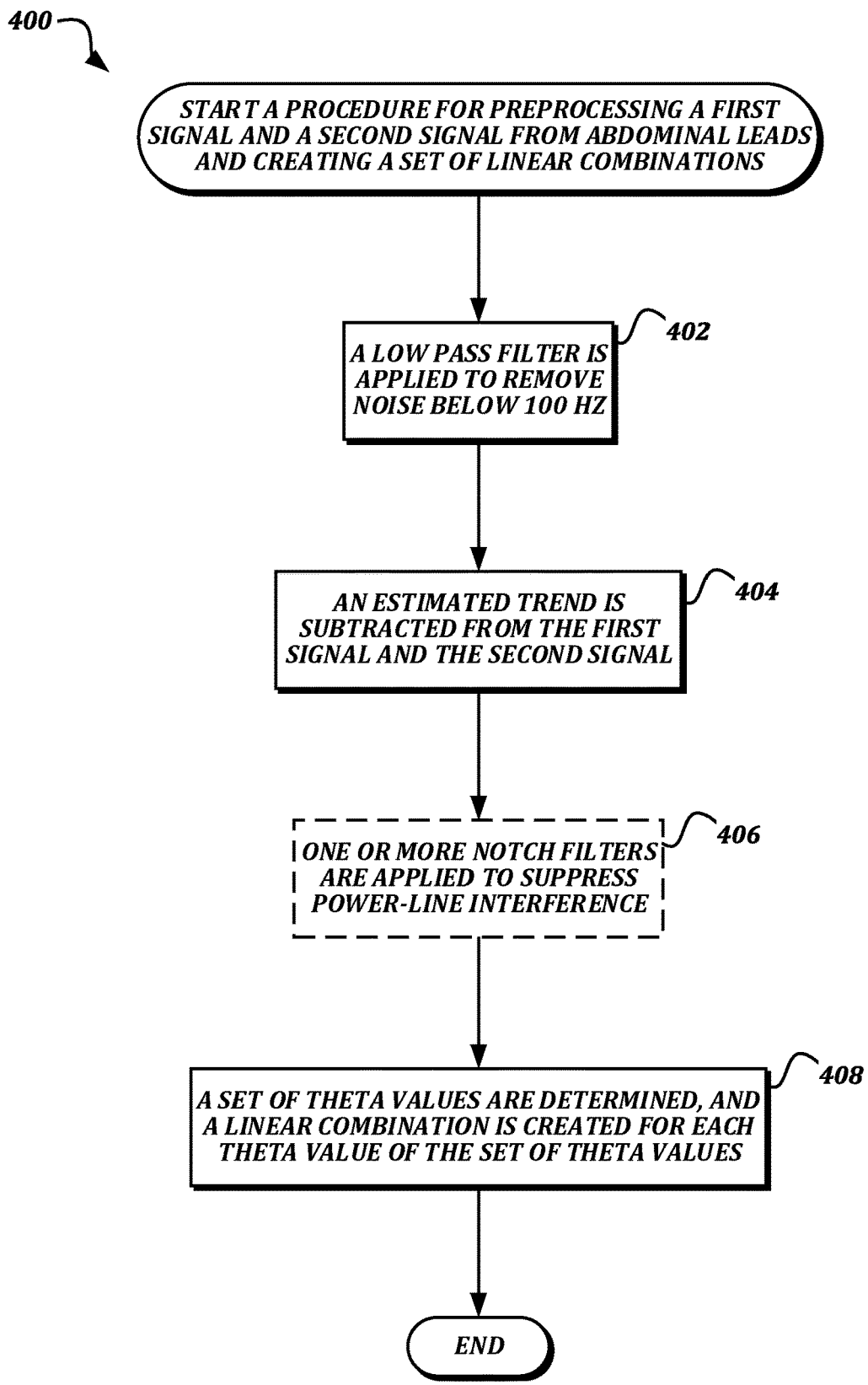
FIG. 4 is a flowchart that illustrates an example embodiment of a procedure for preprocessing a first signal and a second signal from maternal abdominal leads and creating a set of linear combinations according to various aspects of the present disclosure.

FIG. 4 is a flowchart that illustrates an example embodiment of a procedure for preprocessing a first signal and a second signal from maternal abdominal leads and creating a set of linear combinations according to various aspects of the present disclosure. The procedure 400 is an example of a procedure suitable for use in block 304 of FIG. 3. The inputs to the procedure 400 are a first signal and a second signal. The first signal is associated with a first maternal abdominal lead 204, and the second signal is associated with a second maternal abdominal lead 204. As illustrated and described, the procedure 400 assumes only two leads 204 are used. In embodiments with more than two leads 204, the procedure 400 may be executed separately for each pair of leads 204. In some embodiments, the actions described in the procedure 400 may be performed by elements of the abdominal ECG device 202 such as the signal preprocessing engine 206, though the discussion below omits specific reference to the signal preprocessing engine 206 for the sake of brevity and clarity.

From a start block, the procedure 400 advances to block 402, where a low pass filter is applied to remove noise below 100 Hz. At block 404, an estimated trend is subtracted from the first signal and the second signal. In some embodiments, the estimated trend is subtracted from $x_0$, $y_0$, where the trends are estimated using a median filter with a window length $L_{MF}$ greater than 0 seconds. The procedure 400 then advances to optional block 406, where one or more notch filters are applied to suppress power-line interference. For example, a notch filter configured to filter out noise at 50 Hz or 60 Hz may be used. As another example, if the source of data used to test the abdominal ECG device 202 is unknown, both 50 Hz and 60 Hz notch filters may be used. In some embodiments notch filters may not be needed, such as if a separate power-line filter is used. Hence, in such embodiments, the actions of optional block 406 may not be performed.

At block 408, a set of theta (θ) values are determined, and a linear combination is created for each theta value of the set of theta values. In some embodiments, the set of theta values may be chosen from the discrete finite subset $\chi \subset (-1,1]$. In some embodiments, the theta values are chosen from x at uniform intervals. In some embodiments, the theta values are chosen from x randomly. A linear combination $z_\theta$ is then calculated for each theta value using the following formula:

$$z_\theta = \theta x + \sqrt{1-\theta^2} y$$

In the formula, x is a time series representing a signal of the first abdominal lead 204, and y is a time series representing a signal of the second abdominal lead 204.

The procedure 408 then advances to an end block and terminates, returning the set of linear combinations that corresponds to the determined set of theta values. In some embodiments, each linear combination may be returned along with an indication of the theta value used to generate the linear combination, and/or an indication of the first abdominal lead 204 and second abdominal lead 204 from which the signals were obtained.

Figure 5:
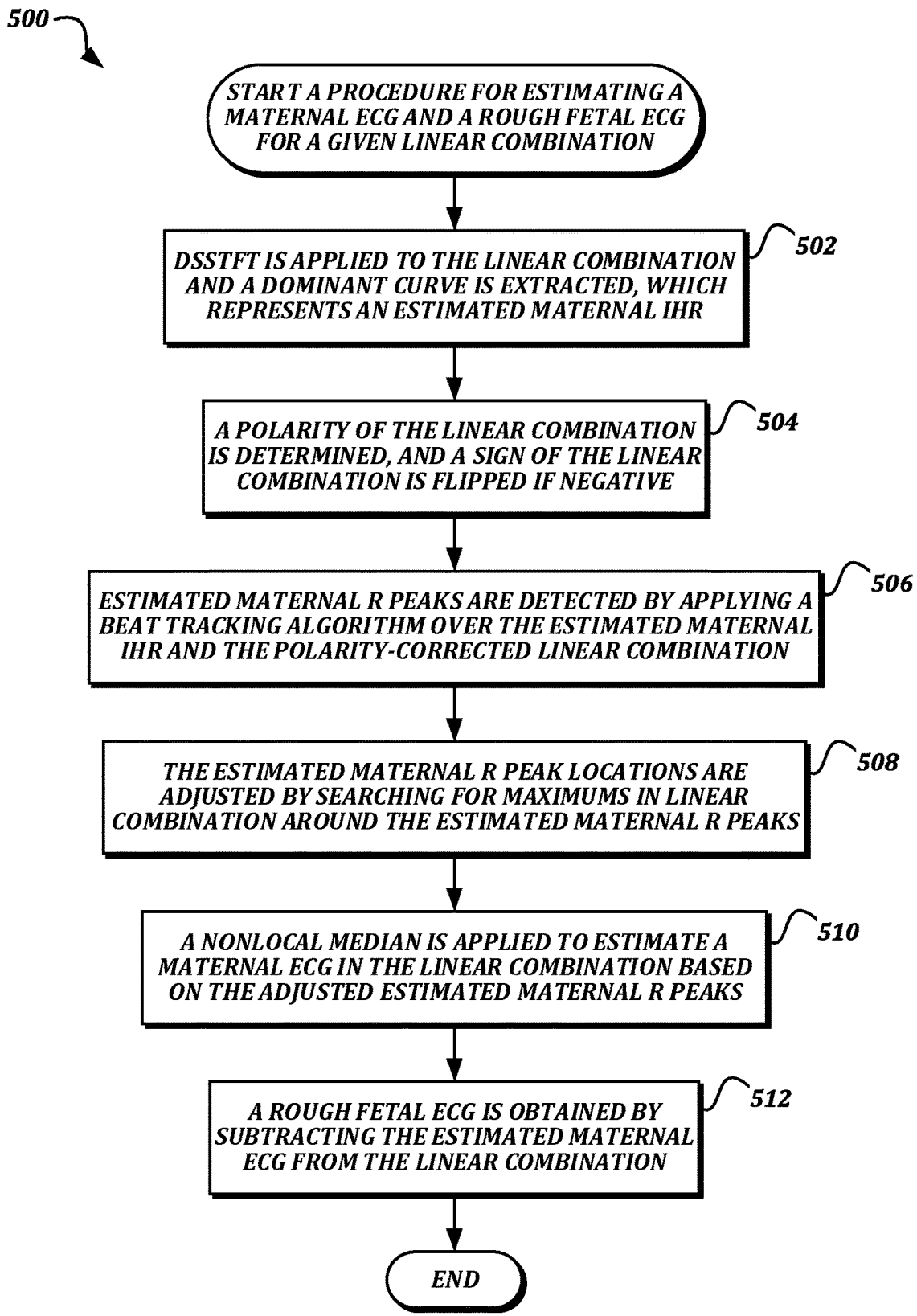
FIG. 5 is a flowchart that illustrates an example embodiment of a procedure for estimating a maternal ECG and a rough fetal ECG for a given linear combination according to various aspects of the present disclosure.

FIG. 5 is a flowchart that illustrates an example embodiment of a procedure for estimating a maternal ECG and a rough fetal ECG for a given linear combination according to various aspects of the present disclosure. The procedure 500 is an example of a procedure suitable for use in block 306 of FIG. 3. The procedure 500 accepts as input a linear combination, such as the linear combinations generated in block 304 of FIG. 3. In some embodiments, the procedure 500 may be executed separately for each linear combination of the set of linear combinations generated in block 304 of FIG. 3. In some embodiments, the actions described in the procedure 500 may be performed by elements of the abdominal ECG device 202 such as the ECG estimation engine 208, though the discussion below omits specific reference to the ECG estimation engine 208 for the sake of brevity and clarity.

From a start block, the procedure 500 advances to block 502, where a de-shape short time Fourier transform (dsSTFT) is applied to the linear combination, and a dominant curve is extracted which represents an estimated maternal instantaneous heart rate (IHR). At block 504, a polarity of the linear combination is determined, and a sign of the linear combination is flipped if negative. That is, if the polarity of the linear combination is negative, the linear combination is multiplied by −1. Next, at block 506, estimated maternal R peaks are detected by applying a beat tracking algorithm over the estimated maternal IHR and the polarity-corrected linear combination. At block 508, the estimated maternal R peak locations are adjusted by searching for maximums in the linear combination around the estimated maternal R peaks. This search may be conducted in a small window around the estimated maternal R peak locations. At block 510, a nonlocal median is applied to estimate a maternal ECG in the linear combination based on the adjusted estimated maternal R peaks. The dsSTFT is described at length in C.-Y. Lin, S. Li, and H.-T. Wu, "Wave-Shape Function Analysis: When Cepstrum Meets Time-Frequency Analysis," Journal of Fourier Analysis and Applications, 2017. Techniques for using a dsSTFT to extract an estimated maternal instantaneous heart rate along with beat tracking algorithms and application of nonlocal medians, are described in L. Su and H.-T. Wu, "Extract Fetal ECG from Single-Lead Abdominal ECG by De-Shape Short Time Fourier Transform and Nonlocal Median," *Frontiers in Applied Mathematics and Statistics,* 22 Feb. 2017. The entire disclosures of these documents are hereby incorporated by reference in their entirety for all purposes.

At block 512, a rough fetal ECG is obtained by subtracting the estimated maternal ECG from the linear combination. In some embodiments, the rough fetal ECG is "rough" in that, at this point in the procedure 500 or method 300, the quality of the fetal ECG for a given linear combination is unknown. The procedure 500 then advances to an end block and terminates, returning at least one of the rough fetal ECG and the estimated maternal ECG as results.

Figure 6:
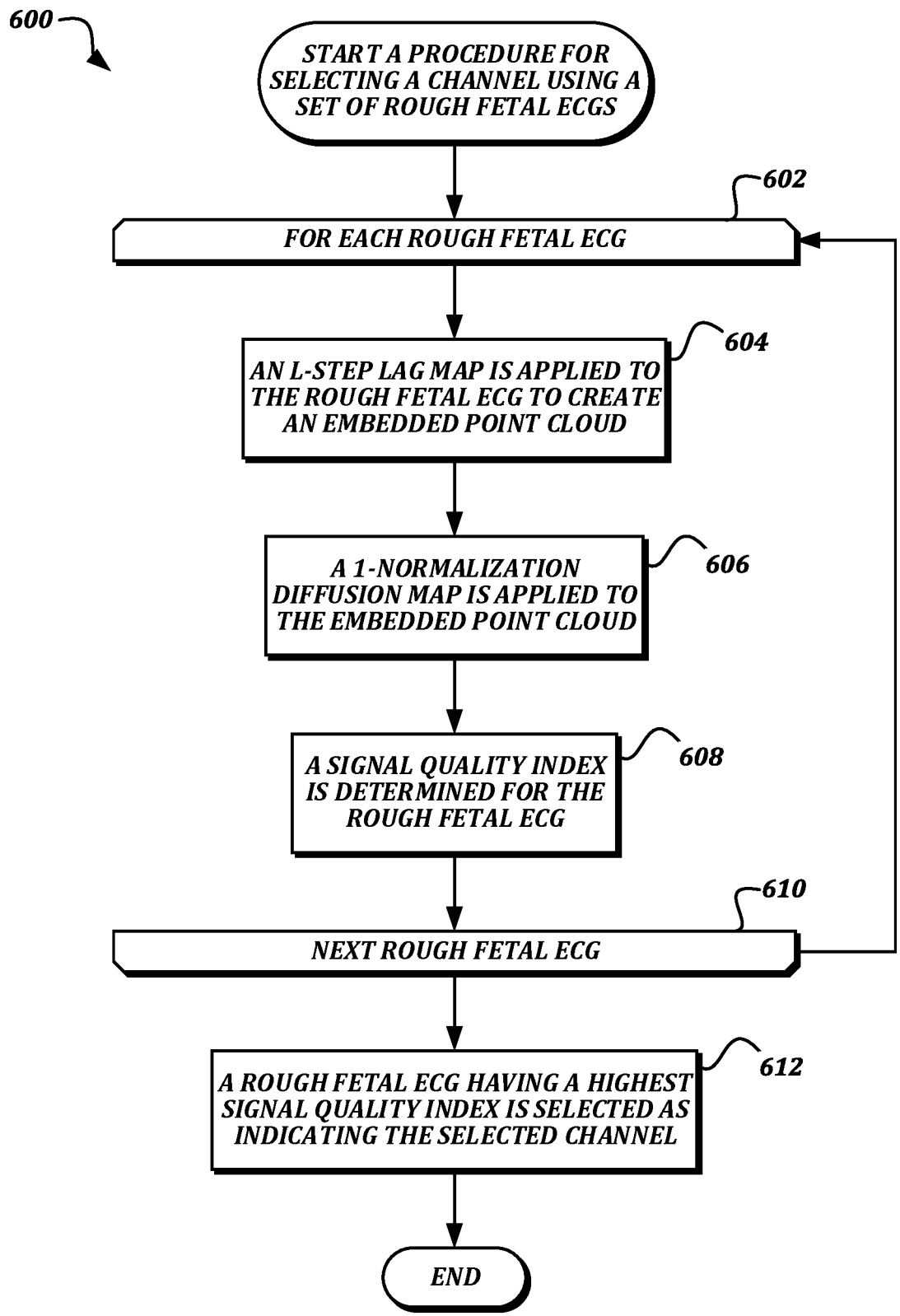
FIG. 6 is a flowchart that illustrates an example embodiment of a procedure for selecting a channel using a set of rough fetal ECGs according to various aspects of the present disclosure.

FIG. 6 is a flowchart that illustrates an example embodiment of a procedure for selecting a channel using a set of rough fetal ECGs according to various aspects of the present disclosure. The procedure 600 is an example of a procedure suitable for use in block 308 of FIG. 3. The procedure 600 accepts as input a rough fetal ECG, such as the rough fetal ECG generated in block 306 of FIG. 3. In some embodiments, a "channel" includes identifications of the two leads and the theta value used to generate a selected linear combination. In some embodiments, a "channel" may also include the rough fetal ECG associated therewith. In some embodiments, the actions described in the procedure 600 may be performed by elements of the abdominal ECG device 202 such as the ECG estimation engine 208, though the discussion below omits specific reference to the ECG estimation engine 208 for the sake of brevity and clarity.

From a start block, the procedure 600 advances to a for loop defined between a for loop start block 602 and a for loop end block 610, which processes each rough fetal ECG. For a given rough fetal ECG, the procedure 600 advances from the for loop start block 602 to block 604, where an L-step lag map is applied to the rough fetal ECG to create an embedded point cloud. The lag map is a method widely applied to study a given time series. In brief, it allows one to reconstruct the structure underlying the time series. For a given time series f of length $N \in \mathbb{N}$, the lag map is a mapping from f to a set of L-dim points, where L is chosen by the user, via:

$$\Psi_{f,L}: i \mapsto (f(i), \ldots, f(i+L))^T \in \mathbb{R}^{L+1}$$

where $i=1, \ldots, N-L$ and the superscript T means taking the transpose. The map $\Psi_{f,L}$ is called the L-step lag map. It has been shown that if f is an observation of a dynamical process whose trajectory is supported on a d-dimensional manifold and L is large enough, then under some weak mathematical conditions, $\Psi_{f,L}$ could recover the manifold up to a diffeomorphism. Since the cardiac activity is periodic, the corresponding underlying manifold is a one-dimensional circle representing the cardiac dynamics that is diffeomorphic to the unit circle $S^1$, and the lag map of the cardiac activity time series leads to a point cloud supported on another one-dimensional simple closed curve.

The above-mentioned important property of the lag map allows one to examine the quality of the reconstructed fECG. If $f \in \mathbb{R}^N$ is the true fECG signal, or a good estimation of the fECG signal, we obtain a one-dimensional simple closed curve by the point cloud:

$$\chi_{f,L} := \{\Psi_{f,L}(i)\}_{i=1}^{N-L} \in \mathbb{R}^{L+1}$$

On the other hand, if the tempted fECG estimator $f \in \mathbb{R}$ fails to be a good estimator of the fECG signal, the point cloud $\chi_{f,L}$ might be away from any one-dimensional simple closed curve. Another important fact is that when f is the fECG signal, the point cloud $\chi_{f,L}$ is in general non-uniformly sampled from the one-dimensional circle. This fact comes from the diffeomorphic relationship between the reconstructed simple closed curve and the underlying simple closed curve via the lag map.

To take this fact into account to examine the quality of the reconstructed fECG via the L-step lag map, one may apply the graph Laplacian (GL), which is the building block of several dimension reduction algorithms, such as the diffusion map (DM). Accordingly, at block 606, a 1-normalization diffusion map is applied to the embedded point cloud. Fix the given embedded point cloud $\chi_{f,L}$. Build a complete affinity graph $G = (V, E, \omega)$ with vertices $V = \chi_{f,L}$ by viewing any pairs of points in $\chi_{f,L}$ as edges; that is:

$$E = \{(\Psi_{f,L}(i), \Psi_{f,L}(j)) | i \neq j\}$$

The affinity function $\omega: E \to \mathbb{R}^+$ is then defined by:

$$\omega(\Psi_{f,L}(i), \Psi_{f,L}(j)) = \exp\left\{-\frac{\|\Psi_{f,L}(i) - \Psi_{f,L}(j)\|^2}{\epsilon}\right\}$$

for $i, j = 1, \ldots, N-L$, $i \neq j$, and $\epsilon > 0$ is the kernel bandwidth chosen by the user. Here, the affinity between $\Psi_{f,L}(i)$ and $\Psi_{f,L}(j)$ is reversely proportional to the distance between $\Psi_{f,L}(i)$ and $\Psi_{f,L}(j)$. Note that while one could choose a more general kernel, here the focus is on the Gaussian kernel to simplify the discussion. In practice, the Gaussian kernel performs well and the dependence on the chosen kernel is marginal. In general, the point cloud might not be uniformly sampled from the geometric object of interest, and the nonuniform sampling effect might generate a negative impact on the upcoming analysis. To resolve this issue, the a-normalization technique is introduced. Take $0 \leq \alpha \leq 1$, one could define an a-normalized affinity function defined on E, denoted as $\omega^{(\alpha)}$, by:

$$\omega^{(\alpha)}(\Psi_{f,L}(i), \Psi_{f,L}(j)) = \frac{\omega(\Psi_{f,L}(i), \Psi_{f,L}(j))}{d_i^\alpha d_j^\alpha}$$

where d is the degree function defined on the vertex set as $$d_i = \sum_{j=1}^{N-L} \omega^{(\alpha)}(\Psi_{f,L}(i), \Psi_{f,L}(j))$$

for $i=1, \ldots, N-L$. When $\alpha=1$, this $\alpha$-normalized affinity could effectively alleviate the impacts introduced by the nonuniform sampling. In the fECG application, as discussed above, $\chi_{f,L}$ is in general non-uniformly sampled from the one-dimensional simple closed curve, so one may apply this $\alpha$-normalization technique.

To define the GL, first, define an $\alpha$-normalized affinity matrix $W^{(\alpha)} \in \mathbb{R}^{(N-L) \times (N-L)}$ by $$W_{ij}^{(\alpha)}(\Psi_{f,L}(i), \Psi_{f,L}(j))$$

for $i, j = 1, \ldots, N-L$, define a diagonal a-normalized degree matrix $D^{(\alpha)} \in \mathbb{R}^{(N-L) \times (N-L)}$ by $$D_{ii}^{(\alpha)} = \sum_{j=1}^{N-L} w_{ij}$$

for $i=1, \ldots, N-L$, and the a-normalized graph Laplacian is then defined by $$L^{(\alpha)} := I - D^{(\alpha)^{-1}} W^{(\alpha)}.$$

Since L is similar to the symmetric matrix $I - D^{(\alpha)^{-1/2}} W^{(\alpha)} D^{(\alpha)^{-1/2}}$, it has a complete set of right eigenvectors $\varphi_1, \ldots, \varphi_{N-L}$ with corresponding eigenvalues $0 = \lambda_1 < \lambda_2 \leq \ldots \leq \lambda_{N-L} \leq 1$. Note that $\varphi_1 = (1, 1, \ldots, 1)^T$ since $D^{(\alpha)^{-1}} W^{(\alpha)}$ is a transition matrix defined on the graph G. It has been shown that if $\chi$ is sampled from a low dimensional Riemannian manifold, when $\alpha = 1$ and $N \to \infty$, asymptotically the eigenvectors $\varphi_i$ converges pointwisely and spectrally to the ith eigenfunction of the Laplace-Beltrami operator of the Riemannian manifold. In general, this allows one to reconstruct the manifold by applying the diffusion geometry and the spectral embedding theory, which is commonly known as the DM algorithm.

At block 608, a signal quality index (SQI) is determined for the rough fetal ECG. In the present application, due to the periodic oscillation intrinsic to the fECG, the $\alpha$-normalized graph Laplacian associated with $\chi_{f,L}$ gives us the Laplace-Beltrami operator over a simple closed curve. It follows that asymptotically, the first two non-trivial eigenvectors are the sine and cosine functions. One could thus take this fact into account and design the signal quality index for the channel selection purpose. In some embodiments, the SQI for a given rough fECG denoted $\tilde{Z}_{\theta,f}$ may be determined in the following way. Apply the L-step lag map to embed the interval $[2, T_{CS}+2]$ seconds of $\tilde{Z}_{\theta,f}$ into $\mathbb{R}^L$, where $T_{CS}>0$ is chosen by the user and 2 is chosen to avoid the boundary effect associated with the window in the dsSTFT approach. Here $T_{CS}$ is chosen to be short enough to guarantee the computational efficiency and to avoid the possibility non-stationarity inherited in the fECG signal, and long enough to capture the periodicity of the fECG. Denote the embedded point cloud as $\chi_{\theta,f} \subset \mathbb{R}^L$. Apply the 1-normalization DM to $\chi_{\theta,f}$, where the bandwidth of the kernel is chosen in the following way. One first sets $\epsilon_0$ to be the smallest value such that each data point has at least one neighbor within the distance $\epsilon_0$. Then one sets the bandwidth to be $2\epsilon_0$. Denote $\varphi_{\theta,1}$ to be the first nontrivial eigenvector of the corresponding graph Laplacian. Compute the power spectrum of $\varphi_{\theta,1}$ denoted as $|\hat{\varphi}_{\theta,1}|^2$. Denote $\xi_{\theta,1}, \xi_{\theta,2}, \ldots, \xi_{\theta,n_{cs}}>0$, where $n_{cs} \in \mathbb{N}$ is the number of peaks chosen by the user, to be the frequencies associated with the highest $n_{CS}$ peaks in $|\hat{\varphi}_{\theta,1}|^2$. Fix $L_{CS}>0$ and denote $\mathcal{J}_\theta := \cup_{j=1}^{n_{CS}}[\xi_{\theta,i}-L_{CS}, \xi_{74,i}+L_{CS}]$. The SQI for the channel selection purpose is thus defined as:

$$S_\theta = \frac{\int_{[0,\xi_0/4) \cap \mathcal{J}_\theta} |\hat{\varphi}_{\theta,1}(\xi)|^2 d\xi}{\int_{[0,\xi_0/2) \setminus \mathcal{J}_\theta} |\hat{\varphi}_{\theta,1}(\xi)|^2 d\xi}$$

Under the assumption that the better the quality of the rough fECG is, the closer the embedded point cloud is to the one-dimensional circle, one knows that the higher the SQI, the better the rough fECG is. More precisely, if the embedded point cloud is close to the one-dimensional circle, the first non-trivial eigenvector should behave like an oscillatory function. With the designed SQI, one may choose the optimal rough fECG as the one with the highest SQI.

The procedure 600 then advances to the for loop end block 610. If more rough fetal ECGs remain to be processed, then the procedure 600 returns to the for loop start block 602 to process the next rough fetal ECG. Otherwise, if all of the rough fetal ECGs have been processed, then the procedure 600 advances to block 612, where a rough fetal ECG having a highest signal quality index is selected as indicating the selected channel. The procedure 600 then proceeds to an end block and terminates, returning the selected channel as a result.

Figure 7:
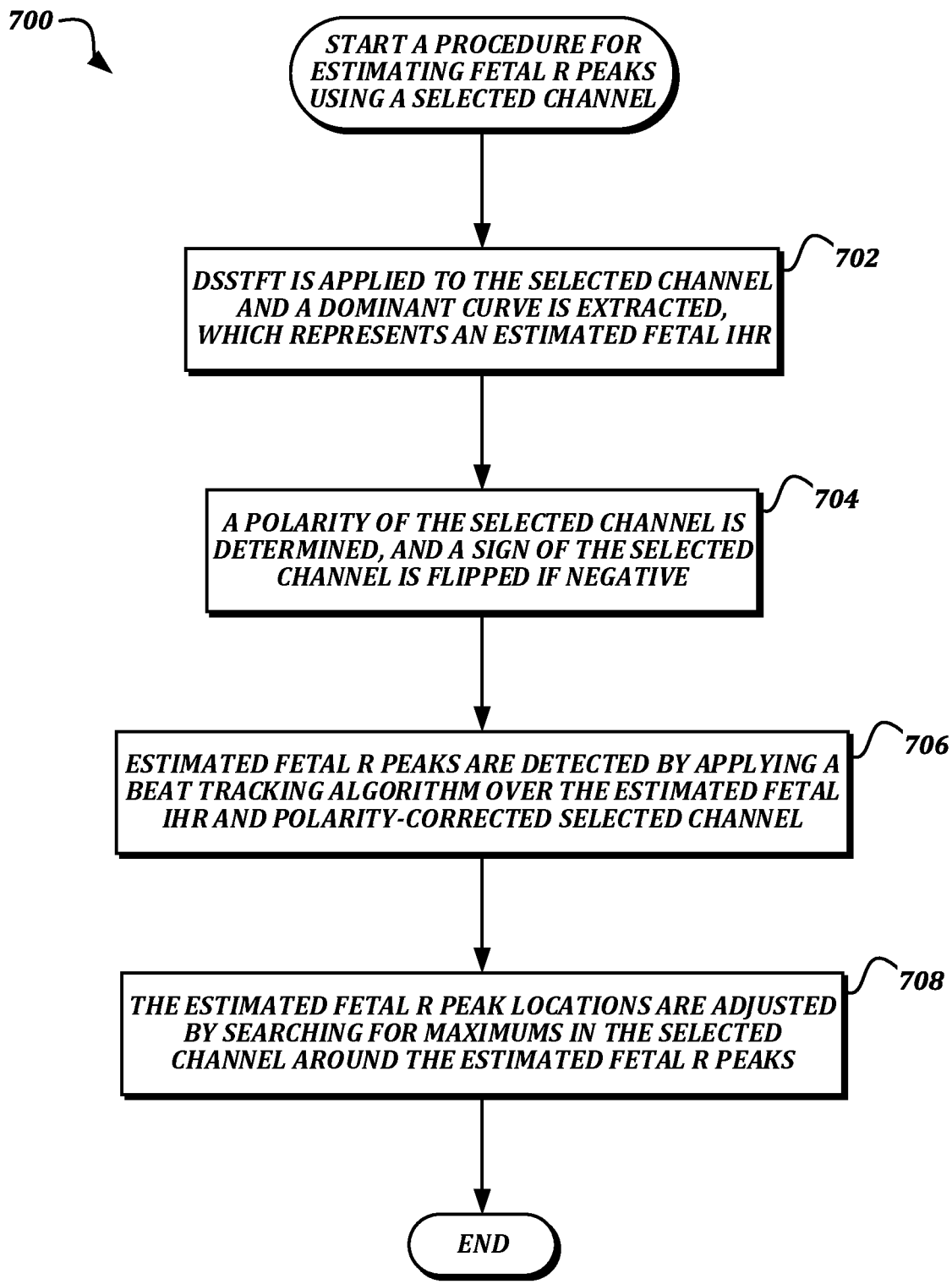
FIG. 7 is a flowchart that illustrates an example embodiment of a procedure for estimating fetal R peaks using a selected channel according to various aspects of the present disclosure.

FIG. 7 is a flowchart that illustrates an example embodiment of a procedure for estimating fetal R peaks using a selected channel according to various aspects of the present disclosure. The procedure 700 is an example of a procedure suitable for use in block 310 of FIG. 3. The procedure accepts as input a channel, which may include the selection of leads and a theta value, and may also include the associated rough fetal ECG derived therefrom. In some embodiments, the actions of procedure 700 are similar to the actions of procedure 500. The actions are repeated here to provide clarity for how the rough fetal ECG is processed, though details of implementation of particular actions may not be repeated here where they are described in more detail above. In some embodiments, the actions described in the procedure 700 may be performed by elements of the abdominal ECG device 202 such as the ECG estimation engine 208, though the discussion below omits specific reference to the ECG estimation engine 208 for the sake of brevity and clarity.

From a start block, the procedure 700 advances to block 702, where dsSTFT is applied to the selected channel and a dominant curve is extracted, which represents an estimated fetal instantaneous heart rate (IHR). At block 704, a polarity of the selected channel is determined, and a sign of the selected channel is flipped if negative. At block 706, estimated fetal R peaks are detected by applying a beat tracking algorithm over the estimated fetal IHR and polarity-corrected selected channel. At block 708, the estimated fetal R peak locations are adjusted by searching for maximums in the selected channel around the estimated fetal R peaks. The procedure 700 then advances to an end block and terminates, returning the adjusted fetal R peak locations as a result.

The above-described techniques were validated using publicly available databases of aECG signals. The first database is the PhysioNet non-invasive fECG database (adfecgdb), where the aECG signals with the annotation provided by experts are publicly available. There are five pregnant women between 38 to 40 weeks of pregnancy in this database. Each has 4 aECG channels and one direct fECG signal recorded from the Komporel system (ITAM Institute, Zabrze, Poland). The four abdominal leads are placed around the navel, a reference lead is placed above the pubic symphysis, and a common mode reference electrode with active-ground signal is placed on the left leg. The signal lasts for 5 minutes and is sampled at a fixed rate 1000 Hz with the 16 bit resolution. The R peak annotation is determined from the direct fECG recorded from the fetal scalp lead.

The second database is the 2013 PhysioNet/Computing in Cardiology Challenge, abbreviated as CinC2013. The validation focused on the set A composed of 75 recordings for an assessment of the SAVER technique since it is the only one with the provided R peak annotation with reference to a direct fECG signal, acquired from a fetal scalp electrode. Each recording includes four noninvasive mECG channels that were obtained from multiple sources using a variety of instrumentations with differing frequency response, resolution, and configurations. Although they are from different resources, all recordings are resampled at the sampling rate 1000 Hz and last for 1 minute. There is no publicly available information about where the leads are placed on the maternal abdomen. Note that some recordings come from the adfecgdb database, but no detail is available publicly. The testing followed the public suggestion to disregard the recording a54 since it was discarded by the Challenge's organizers, and focus instead on the remaining 74 recordings.

In the whole analysis, the R peak detection result is evaluated by beat-to-beat comparisons between the detected beats and the provided annotations. The validation used a matching window of 50 ms. Denote TP, FP, and FN to be true positive rate, false positive rate, and false negative rate, where TP means correctly detected peaks, FP means non-existent peaks that were falsely detected, and FN means existing peaks that were not detected.

The validation reports the sensitivity (SE) and the positive predictive value (PPV) defined as $$SE := \frac{TP}{TP+FN}, PPV = \frac{TP}{TP+FP}$$

and the $F_1$ score, which is the harmonic mean of PPV and SE, $$F_1 := \frac{2TP}{2TP + FN + FP}.$$

The validation also reports the mean absolute error (MAE) of the estimated R peak locations, and report the MAE only on true positive annotations to make the evaluation independent of the detection accuracy. Thus, the MAE is defined as $$MAE := \frac{1}{n_{TP}} \sum_{j=1}^{n_{TP}} |r_i^f - \tilde{r}_i^f|$$

where $n_{TP}$ is the number of true positive annotations, and $\tilde{r}_i^f$ and $r_i^f$ are the temporal location of the i-th true positive reference R-peak and temporal location of the i-th true positive detected R peak.

For each database, the validation reports two sets of statistics. First, for each subject, the best $F_1$ result is recorded among all pairs of available channels, denoted as $F_1(1)$ and report the mean and median of the $F_1(1)$ of all subjects, and the corresponding summary statistics of the MAE, denoted as MAE(1). To see how stable the algorithm is, the validation also records the median $F_1$ result among all pairs of available channels, called $F_1(0.5)$, and reports the mean and median of the $F_1(0.5)$ of all subjects, as well as the corresponding summary statistics of the MAE, denoted as MAE(0.5).

Second, to evaluate the lead placement issue, for each pair of available channels, the validation reports the mean and median of the $F_1$ of all subjects, and the corresponding summary statistics of the MAE. To avoid the boundary effect inevitable in the dsSTFT algorithm due to the window length, the first and last 2 seconds in every recording are not evaluated. The notation a±b indicates the mean a with the standard deviation b.

For a fair comparison and the reproducibility purposes, the parameters used for SAVER in the validation are listed below. One of ordinary skill in the art will recognize that these parameters are examples only, and that in some embodiments, other parameters may be used. For the linear combination of two channels, $\chi$ is set using $\chi = \{-1 + k/6\}_{k=1}^{12}$. The window length $L_{MF}$ of the median filter for the baseline wandering removal is chosen to be 0.1 second. For the dsSTFT, the beat tracking, and the nonlocal median, the parameters are set to be the same as those reported in the paper incorporated by reference above: the window h is chosen to be the Hamming window of length 5s, the up-sampling rate $\alpha=10$, the frequency resolution is set to 0.02 Hz, the quefrency resolution is set to 10 ms, and $v=10^{-4}\%$ of the root mean square energy of the signal under analysis for the dsSTFT. In the beat tracking, $\lambda_{BT}$ is set to 50. In the nonlocal median, we choose $K_m = K_f = 40$.

For the channel selection, the lag is set to L=7 for the lag map; the Gaussian kernel and $\alpha=1$ normalization are chosen for the DM; $T_{CS}=40$, $n_{CS}=6$, and $L_{CS}=0.1375$ Hz are chosen for the adfecgdb database, and $T_{CS}=10$, $n_{CS}=6$ and $L_{CS}=0.25$ Hz are chosen for the CinC database. While these parameters were chosen in an ad-hoc fashion without any optimization pursue, those parameters could be optimized based on the application field and the environment. The techniques were tested on a MacBook Air (13-inch, Mid 2013) with Processor 1.3 GHz Intel Core i5, Memory 4 GB1600 MHz DDR3, Mac OS Sierra (Version 10.12.2), and Matlab R2015b without implementing the parallel computation. For the adfecgdb database, the direct fECG measurement was lost between 187 and 191s and between 203 and 211s in the r10 record, and these two segments were discarded in the evaluation.

The evaluation results of the above technique for each combination of two channels out of four available channels of all subjects in the adfecgdb database are shown in FIG. 8 for a clear comparison purpose. Except the combination of Channel 2 and Channel 3 in r01 and r08, all the other combinations have the $F_1$ consistently greater than 94%. For the MAE, the result is always smaller than 9 ms except the combination of Channel 2 and Channel 3 in r08. FIG. 9 shows the comparison of the proposed SAVER technique with other available algorithms. The $F_1(1)$ and $F_1(0.5)$ of all 6 pairs for each subject are recorded, and the summary statistics of all subjects are shown. It is clear that SAVER is consistently better than the other algorithms. The average running time is 141.55s for SAVER, 194.44s for the ds-AF-LMS, 589.83s for the ds-AF-ESN, 10.01s for JADE-ICA, and 10.98s for PCA.

For the CinC2013 database, in FIG. 10 SAVER is compared with the other available techniques in the CinC2013 database. The $F_1(1)$ of all recordings of SAVER is 92.99±16.0% and the corresponding MAE(1) is 5.38±4.52 msec, which are both better than the other compared methods. The median $F_1(0.5)$ of all recordings of SAVER is 85.44 ±22.42% and the MAE(0.5) of SAVER is 6.54 ±4.92 msec, which are both better than the best result determined by other methods. It should be noted that the median of $F_1(0.5)$ over 6 pairs of SAVER is still as high as 96.32%, while other methods decline dramatically to less than 60%. This result suggests the stability of the proposed method.

The average running time is 20.29s for SAVER, 27.26s for the ds-AF-LMS, 100.35s for the ds-ESN, 3.29s for JADE-ICA, and 3.20s for PCA.

To further evaluate the influence of the lead placement, or to answer if a best lead placement scheme for the proposed two-channel algorithm could be determined, summary statistics of all pairs of two channels for the adfecgdb database are reported in FIG. 11 and the CinC2013 database in FIG. 12. It is interesting to see that for the adfecgdb database, except for the combination of channel 2 and channel 3, the mean $F_1$ accuracy is greater than 97%. The outlier of the combination of channel 2 and channel 3 comes from the fact that the fECG is strong in case r08, which confuses the channel selection step. As a result, SAVER extracts the maternal ECG as the fECG, which leads to a wrong fECG estimation. While determining the role of each component is a common issue for the fetal-maternal ECG separation techniques and commonly one needs more information to handle it, we leave this open problem for the future work.

Compared with the result of the adfecgdb database, the performance of SAVER in the CinC2013 database is not uniform cross different combinations of channels. Note that the lead placement scheme is unknown for the CinC2013 database, so it is not possible to conclude which pair of channels is the best. However, if we assume that the lead placement scheme for all recordings in the CinC2013 database is the same as the lead placement scheme shown in FIG. 2, then the CinC2013 database results suggest that the best combination is channel 1 and channel 4; the $F_1$ has the mean of 87.93% with the standard deviation 22.64%, and the median 97.60% with the interquartile range 6.92%; the MAE has the mean of 6.21 ms with the standard deviation 6.03 ms, and the median 4.34 ms with the interquartile range 5.62 ms.

Another finding deserves a discussion is that unlike the adfecgdb database, one can see the discrepancy between the best $F_1$ out of the 6 pairs reported in FIG. 10 and the average $F_1$ of each pair reported in FIG. 12. This might suggest that the lead system applied in the CinC2013 database is heterogenous across the recordings. For the adfecgdb database, the result is overall compatible with, or better than, the state-of-art result reported in the field. For example, if one chooses the pair of channel 1 and channel 2, the result is better than the best channel result based on the continuous wavelet transform based single-channel algorithm. However, it is not a fair comparison since the technique used in the previous work is a single channel technique. On the other hand, if one compares with the methods based on ICA on four channels, our result is compatible. The MAE, which is less reported in the literature, is as small as 10 msec, which indicates the potential of applying SAVER to do the fetal heart rate variability (HRV) analysis.

For the CinC2013 database, the result using SAVER is compatible, or better than, the reported results. At the first glance, it is not the case, since by the ICA-based algorithms, the accuracy could be as high as have the mean $F_1$=96%, under the same setup that a detected R-peak was labelled as TP if within 50 ms of a reference Rpeak. However, unlike SAVER, these algorithms are ICA-based and four channels are simultaneously used. Specifically, among different combinations of different algorithms, the algorithm FUSE-SMOOTH achieved the best result—the mean $F_1$ over all recordings is 96%, after removing a33, a38, a47, a52, a54, a71, and a74; the augmentation, the ICA, the template adaptation or extended Kalman filter, and other techniques are applied, and the result with the mean $F_1$=97.3% over all recordings with the standard deviation 0.108 is reported based on the template adaptation, after removing a54. SAVER, on the other hand, outperforms the technique based on four channels and the PCA. The accuracy of such a proposed algorithm in detecting the fetal heart beats gives the mean $F_1$=89.8% over all recordings, under the setup that a detected R-peak was labelled as TP if within 100 ms of a reference R-peak and removing 9 recordings, including a29, a38, a54, a56, a33, a47, a52, a71, and a74. Another novel method based on the channel selection over 4 channels followed by the sequential total variation denoising leads to the accuracy with $F_1$=89.9% and the MAE=9.3 ms under the setup that a detected R-peak was labelled as TP if within 50 ms of a reference R-peak and removing a33, a38, a47, a52, a54, a71, and a74. While SAVER algorithm does not outperform some of the above-mentioned techniques, based on two channels, SAVER leads to the MAE as small as 6.21 ms in channel 1 and channel 4 combination in the CinC2013 database, which again indicates the potential of applying the SAVER to do the fetal HRV analysis.

The encouraging results of SAVER indicate the possibility to design a "two-lead system" for the noninvasive, and long term fECG monitoring purpose. As discussed above, theoretically, the chance is low that the fetal cardiac axis orientation would be so much orthogonal to the 2-dim affine subspace spanned by the two leads that no fECG shape can be reconstructed. This is a big advantage compared with the single-lead system, as the chance that the fetal cardiac axis orientation is orthogonal to the 1-dim affine subspace spanned by the single lead is much higher. Thus, while there have been several successful techniques for the one aECG channel, if the recorded one channel signal does not have fECG information, there is nothing such techniques can do. From the practical viewpoint, since only two leads are needed, the corresponding hardware could be lighter and more deployable than the currently available four-lead or multiple-lead systems. While it is certainly possible to generalize SAVER to systems that use any number of two or more leads (and the technique can be changed directly according to the setup), to have a better balance between the prediction accuracy, the hardware design, and practical purposes, the two-lead system may have advantages.

Figure 13:
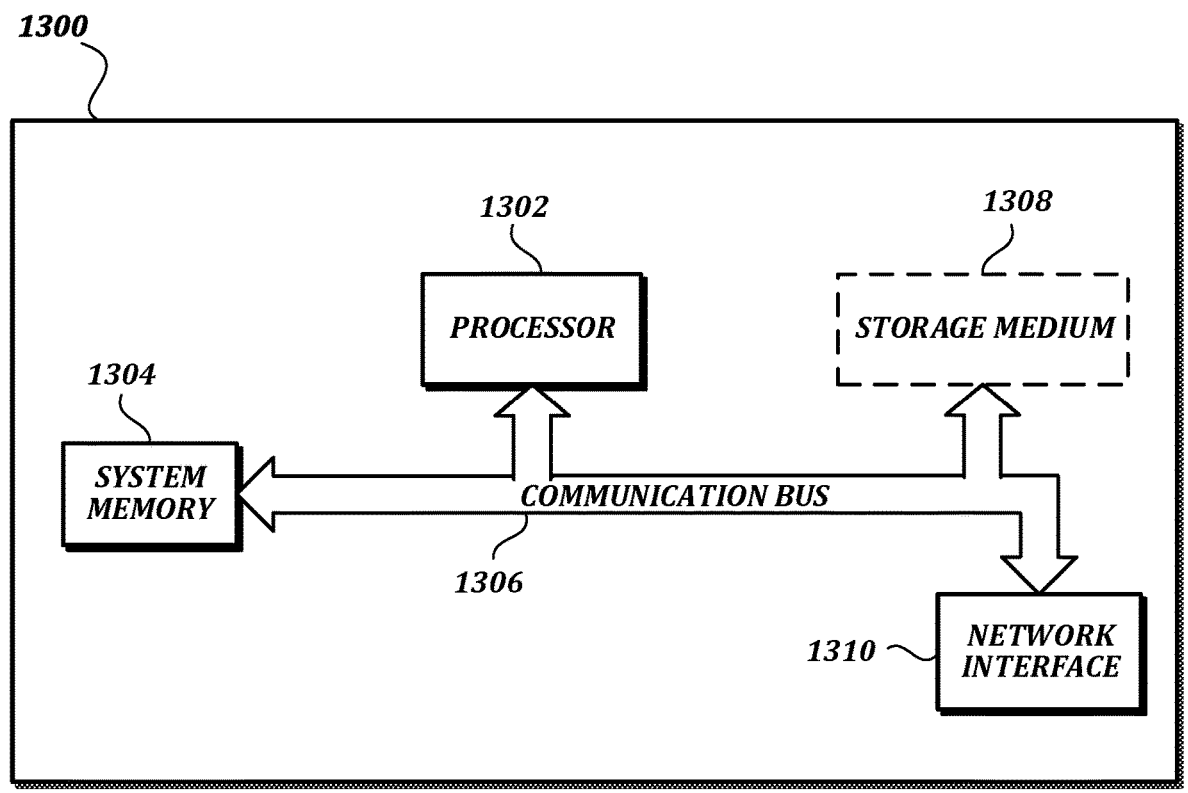
FIG. 13 is a block diagram that illustrates aspects of an exemplary computing device appropriate for use as a computing device of the present disclosure.

FIG. 13 is a block diagram that illustrates aspects of an exemplary computing device 1300 appropriate for use as a computing device of the present disclosure. While multiple different types of computing devices were discussed above, the exemplary computing device 1300 describes various elements that are common to many different types of computing devices. While FIG. 13 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 1300 may be any one of any number of currently available or yet to be developed devices.

In its most basic configuration, the computing device 1300 includes at least one processor 1302 and a system memory 1304 connected by a communication bus 1306. Depending on the exact configuration and type of device, the system memory 1304 may be volatile or nonvolatile memory, such as read only memory ("ROM"), random access memory ("RAM"), EEPROM, flash memory, or similar memory technology. Those of ordinary skill in the art and others will recognize that system memory 1304 typically stores data and/or program modules that are immediately accessible to and/or currently being operated on by the processor 1302. In this regard, the processor 1302 may serve as a computational center of the computing device 1300 by supporting the execution of instructions.

As further illustrated in FIG. 13, the computing device 1300 may include a network interface 1310 comprising one or more components for communicating with other devices over a network. Embodiments of the present disclosure may access basic services that utilize the network interface 1310 to perform communications using common network protocols. The network interface 1310 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 1310 illustrated in FIG. 13 may represent one or more wireless interfaces or physical communication interfaces described and illustrated above with respect to particular components of the system 100.

In the exemplary embodiment depicted in FIG. 13, the computing device 1300 also includes a storage medium 1308. However, services may be accessed using a computing device that does not include means for persisting data to a local storage medium. Therefore, the storage medium 1308 depicted in FIG. 13 is represented with a dashed line to indicate that the storage medium 1308 is optional. In any event, the storage medium 1308 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like. As used herein, the term "computer-readable medium" includes volatile and non-volatile and removable and non-removable media implemented in any method or technology capable of storing information, such as computer readable instructions, data structures, program modules, or other data. In this regard, the system memory 1304 and storage medium 1308 depicted in FIG. 13 are merely examples of computer-readable media.

Suitable implementations of computing devices that include a processor 1302, system memory 1304, communication bus 1306, storage medium 1308, and network interface 1310 are known and commercially available. For ease of illustration and because it is not important for an understanding of the claimed subject matter, FIG. 13 does not show some of the typical components of many computing devices.

In this regard, the computing device 1300 may include input devices, such as a keyboard, keypad, mouse, microphone, touch input device, touch screen, tablet, and/or the like. Such input devices may be coupled to the computing device 1300 by wired or wireless connections including RF, infrared, serial, parallel, Bluetooth, Bluetooth low energy, USB, or other suitable connections protocols using wireless or physical connections.

Similarly, the computing device 1300 may also include output devices such as a display, speakers, printer, etc. Since these devices are well known in the art, they are not illustrated or described further herein.

As used herein and unless otherwise indicated, the terms "a" and "an" are taken to mean "one", "at least one" or "one or more". Unless otherwise required by context, singular terms used herein shall include pluralities and plural terms shall include the singular. Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The embodiments of the invention in which an exclusive property or privilege is claimed are defined as follows:

1. A system for non-invasive measurement of heartbeat characteristics, the system comprising:
   a set of maternal abdominal leads, including a first maternal abdominal lead and a second maternal abdominal lead; and
   an abdominal electrocardiogram (aECG) device communicatively coupled to the maternal abdominal leads, comprising at least one processor and a non-transitory computer-readable medium, wherein the non-transitory computer-readable medium has instructions stored thereon that, in response to execution by the at least one processor, cause the aECG device to measure heartbeat characteristics by:
   creating a set of linear combinations using signals from the set of maternal abdominal leads, wherein each linear combination includes a pair of selected leads from the set of maternal abdominal leads and a θ value usable to linearly combine signals from the pair of selected leads;
   determining a set of rough fECGs based on the set of linear combinations;
   selecting a channel based on the set of rough fECGs, wherein the channel includes the pair of selected leads and the θ value of a linear combination; and
   measuring the heartbeat characteristics using the selected channel.

2. The system of claim 1, wherein the heartbeat characteristics are fetal R peaks or a fetal heart rate.

3. The system of claim 1, wherein the instructions further cause the aECG device to preprocess the signals from the set of maternal abdominal leads by performing at least one of applying a low pass filter, applying one or more notch filters to suppress power line interference, and subtracting an estimated trend.

4. The system of claim 1, wherein creating the set of linear combinations includes:
   determining a set of θ values; and
   for each θ value of the set of θ values, create a linear combination $z_\theta$ as:

$$z_\theta = \theta x + \sqrt{1-\theta^2} y$$

wherein x is a time series representing a signal of the first maternal abdominal lead, and y is a time series representing a signal of the second maternal abdominal lead.

5. The system of claim 1, wherein the set of maternal abdominal leads further includes at least a third abdominal lead, and wherein creating the set of linear combinations includes:
   determining a pair of leads from the set of maternal abdominal leads;
   determining a set of θ values; and
   for each θ value of the set of θ values, create a linear combination $z_\theta$ as:

$$z_\theta = \theta x + \sqrt{1-\theta^2} y$$

wherein x is a time series representing a signal of a first lead of the pair of leads, and y is a time series representing a signal of a second lead of the pair of leads.

6. The system of claim 5, wherein creating the set of linear combinations further includes:
   determining a new pair of leads from the set of maternal abdominal leads;
   creating a linear combination for the new pair of leads for each θ value of the set of θ values; and
   repeating the actions of determining a new pair of leads and creating a linear combination for the new pair of leads for each θ value of the set of θ values for each pairwise combination of leads in the set of maternal abdominal leads.

7. The system of claim 1, wherein determining a set of rough fECGs includes, for each linear combination of the set of linear combinations:
   estimating a maternal ECG based on the linear combination; and
   subtracting the estimated maternal ECG from the linear combination.

8. The system of claim 7, wherein estimating a maternal ECG based on the linear combination includes at least one of storing the maternal ECG in an ECG data store and presenting the maternal ECG on a display device.

9. The system of claim 7, wherein estimating a maternal ECG based on the linear combination includes:
   applying a de-shape short time Fourier transform (dsSTFT) to the linear combination and extracting the dominant curve to obtain an estimated maternal instantaneous heart rate (IHR);
   determining a polarity of the linear combination and multiplying the linear combination by −1 if the determined polarity is negative to create a polarity-corrected linear combination;
   computing locations of maternal R-peaks using the estimated maternal IHR and the polarity-corrected linear combination;
   adjusting the computed locations of the maternal R-peaks by searching for a maximum in the polarity-corrected linear combination around each computed location; and
   applying the nonlocal median to estimate the maternal ECG in the linear combination based on the adjusted maternal R-peak locations.

10. The system of claim 1, wherein selecting a channel includes:
    determining a signal quality index (SQI) for each rough fECG of the set of rough fECGs; and
    selecting a channel associated with a rough fECG having a highest SQI.

11. The system of claim 10, wherein the SQI is determined by:
    applying an L-step lag map to the rough fECG to create an embedded point cloud $\chi_{\theta,f}$;
    applying a 1-normalization diffusion map to $\chi_{\theta,f}$ and determining the SQI $S_\theta$ as:

$$S_\theta = \frac{\int_{[0,\xi_0/4)\cap \mathcal{J}_\theta} |\hat{\phi}_{\theta,1}(\xi)|^2 d\xi}{\int_{[0,\xi_0/2)\setminus \mathcal{J}_\theta} |\hat{\phi}_{\theta,1}(\xi)|^2 d\xi}$$

wherein $\phi_{\theta,1}$ is a first nontrivial eigenvector of a corresponding graph Laplacian;
    wherein $|\hat{\phi}_{\theta,1}|^2$ is a power spectrum of $\phi_{\theta,1}$;
    wherein $\xi_{\theta,1}, \xi_{\theta,2}, \ldots, \xi_{\theta,n_{cs}} > 0$, where $n_{cs} \in \mathbb{N}$ is a number of peaks chosen by a user to be frequencies associated with highest $n_{cs}$ peaks in $|\hat{\phi}_{\theta,1}|^2$;
    wherein $L_{cs} > 0$; and
    wherein $\mathcal{J}_\theta := \cup_{j=1}^{n_{cs}} [\xi_{\theta,i} - L_{cs}, \xi_{\theta,i} + L_{cs}]$.

12. A non-transitory computer-readable medium, wherein the non-transitory computer-readable medium has computer-executable instructions stored thereon that, in response to execution by at least one processor of an abdominal electrocardiogram (aECG) device, cause the aECG device to measure heartbeat characteristics by:
    creating a set of linear combinations using signals from a first maternal abdominal lead and a second maternal abdominal lead, wherein each linear combination includes a pair of selected leads from the set of maternal abdominal leads and a θ value usable to linearly combine signals from the pair of selected leads;
    determining a set of rough fECGs based on the set of linear combinations;
    selecting a channel based on the set of rough fECGs, wherein the channel includes the pair of selected leads and the θ value of a linear combination; and
    measuring the heartbeat characteristics using the selected channel.

13. The computer-readable medium of claim 12, wherein the heartbeat characteristics are fetal R peaks or a fetal heart rate.

14. The computer-readable medium of claim 12, wherein the instructions further cause the aECG device to preprocess the signals from the abdominal leads by performing at least one of applying a low pass filter, applying one or more notch filters to suppress power line interference, and subtracting an estimated trend.

15. The computer-readable medium of claim 12, wherein creating the set of linear combinations includes:
    determining a set of θ values; and
    for each θ value of the set of θ values, create a linear combination $z_\theta$ as:

$$z_\theta = \theta x + \sqrt{1-\theta^2} y$$

wherein x is a time series representing a signal of the first abdominal lead, and y is a time series representing a signal of the second abdominal lead.

16. The computer-readable medium of claim 15, wherein creating the set of linear combinations includes:
    receiving a third signal from a third maternal abdominal lead; and
    for each θ value of the set of θ values, create a linear combination $z_\theta$ as:

$$z_\theta = \theta x + \sqrt{1-\theta^2} y'$$

wherein x is a time series representing a signal of the first abdominal lead, and y' is a time series representing a signal of the second abdominal lead.

17. The computer-readable medium of claim 12, wherein determining a set of rough fECGs includes, for each linear combination of the set of linear combinations:
    estimating a maternal ECG based on the linear combination; and
    subtracting the estimated maternal ECG from the linear combination; and
    wherein the actions further comprise at least one of storing the maternal ECG in an ECG data store and presenting the maternal ECG on a display device.

18. The computer-readable medium of claim 17, wherein estimating a maternal ECG based on the linear combination includes:
- applying a de-shape short time Fourier transform (dsSTFT) to the linear combination and extracting the dominant curve to obtain an estimated maternal instantaneous heart rate (IHR);
- determining a polarity of the linear combination and multiplying the linear combination by −1 if the determined polarity is negative to create a polarity-corrected linear combination;
- computing locations of maternal R-peaks using the estimated maternal IHR and the polarity-corrected linear combination;
- adjusting the computed locations of the maternal R-peaks by searching for a maximum in the polarity-corrected linear combination around each computed location; and
- applying the nonlocal median to estimate the maternal ECG in the linear combination based on the adjusted maternal R-peak locations.

19. The computer-readable medium of claim 12, wherein selecting a channel includes:
- determining a signal quality index (SQI) for each rough fECG of the set of rough fECGs; and
- selecting a channel associated with a rough fECG having a highest SQI.

20. The computer-readable medium of claim 19, wherein the SQI is determined by:
- applying an L-step lag map to the rough fECG to create an embedded point cloud $\chi_{\theta,f}$;
- applying a 1-normalization diffusion map to $\chi_{\theta,f}$ and determining the SQI $S_\theta$ as:

$$S_\theta = \frac{\int_{[0,\xi_0/4] \cap \mathcal{J}_\theta} |\hat{\phi}_{\theta,1}(\xi)|^2 d\xi}{\int_{[0,\xi_0/2] \setminus \mathcal{J}_\theta} |\hat{\phi}_{\theta,1}(\xi)|^2 d\xi}$$

wherein $\phi_{\theta,1}$ is a first nontrivial eigenvector of a corresponding graph Laplacian;
wherein $|\hat{\phi}_{\theta,1}|^2$ is a power spectrum of $\phi_{\theta,1}$;
wherein $\xi_{\theta,1}, \xi_{\theta,2}, \ldots, \xi_{\theta,n_{cs}} > 0$, where $n_{cs} \in \mathbb{N}$ is a number of peaks chosen by a user to be frequencies associated with highest $n_{cs}$ peaks in $|\hat{\phi}_{\theta,1}|^2$;
wherein $L_{cs} > 0$; and
wherein $\mathcal{J}_\theta := \cup_{j=1}^{n_{cs}} [\xi_{\theta,i} - L_{CS}, \xi_{74,i} + L_{CS}]$.

* * * * *